(12) United States Patent
Holve

(10) Patent No.: US 7,782,459 B2
(45) Date of Patent: Aug. 24, 2010

(54) LASER-BASED APPARATUS AND METHOD FOR MEASURING AGGLOMERATE CONCENTRATION AND MEAN AGGLOMERATE SIZE

(75) Inventor: Donald John Holve, Berkeley, CA (US)

(73) Assignee: Process Metrix, Pleasanton, CA (US)

( * ) Notice: Subject to any disclaimer, the term of this patent is extended or adjusted under 35 U.S.C. 154(b) by 239 days.

(21) Appl. No.: 12/143,081

(22) Filed: Jun. 20, 2008

(65) Prior Publication Data

US 2009/0079981 A1 Mar. 26, 2009

Related U.S. Application Data

(60) Provisional application No. 60/994,995, filed on Sep. 24, 2007.

(51) Int. Cl.
*G01N 15/02* (2006.01)
(52) U.S. Cl. ...................................... 356/336
(58) Field of Classification Search ................ None
See application file for complete search history.

(56) References Cited

U.S. PATENT DOCUMENTS

| | | |
|---|---|---|
| 4,110,044 A | 8/1978 | Pettersson et al. |
| 4,420,256 A | 12/1983 | Fladda et al. |
| 4,752,131 A | 6/1988 | Eisenlauer et al. |
| 5,194,921 A | 3/1993 | Tambo et al. |
| 5,578,995 A | 11/1996 | Bryant et al. |
| 6,042,249 A * | 3/2000 | Spangenberg ............... 362/259 |
| 6,055,052 A | 4/2000 | Lilienfeld |
| 7,619,731 B2 * | 11/2009 | Lally et al. ............... 356/237.5 |

FOREIGN PATENT DOCUMENTS

| | | |
|---|---|---|
| EP | 0485817 | 5/1992 |
| EP | 0992786 | 4/2000 |
| EP | 1760449 | 3/2007 |
| GB | 2226880 | 7/1990 |

OTHER PUBLICATIONS

De Luliis, S., Cignoli, F., Benecchi, Zizak, G. "Determination of Soot Parameters by a Two-angle Scattering-extinction Technique in an Ethylene Diffusion Flame," Applied Optics, 37(33): 7865-7874 (1998).
Sorensen, C.M., "Light Scattering by Fractal Aggregates: A Review", Aerosol Sci. and Tech. 35: 648-687 (2001).

(Continued)

*Primary Examiner*—Tu T Nguyen
(74) *Attorney, Agent, or Firm*—Mardson Q. McQuay

(57) ABSTRACT

Apparatuses, methods, and systems for measuring mean particle size and concentration of a polydispersion of agglomerates are disclosed. In one embodiment, the apparatuses include a light source; a focusing lens to form a probe volume; a first light detector positioned at a first angular position from the beam of light; and a second light detector positioned at a second angular position from the first direction of the beam of light, the mean particle size and concentration being determined using nearly invariant functions of a ratio of the light scattered measured by the first and second detectors.

49 Claims, 19 Drawing Sheets

OTHER PUBLICATIONS

Neer, A., and Koylu, U., "Effect of Operating Conditions on the Size, morphology, and concentration of Submicrometer Particulates Emitted from a Diesel Engine" Combustion and Flame, 146: 142-154 (2006).

Hu, B., and Koylu, U., "Size and Morphology of Soot Particulates Sampled from a Turbulent Nonpremixed Acetylene Flame", Aerosol Science and Technology, 38: 1009-1018 (2004).

Koylu, U.O., Faeth, G.M., Farias, T.L., and Carvalho, M.G., "Fractal and Projected Structure Properties of Soot Aggregates," Combustion and Flame 100: 621-633 (1995).

Sorensen, C. and Feke, G. "The Morphology of Macroscopic Soot," Aerosol Sci. and Technology, 25: 328-327 (1996).

Brasil, A.M., Farias, T.L., and Carvalho, M.G., "Evaluation of the Fractal Properties of Cluster-Cluster Aggregates," Aerosol Science and Technology 33: 440-454 (2000).

Hu, B., Yang, B., and Koylu, U., "Soot Measurements at the Axis of an Ethylene/air Non-premixed Turbulent Jet Flame," Combustion and Flame, 134: 93-106 (2003).

Slowik, J., Stainken, K., Davidovits, P., Williams, L., Jayne, J., Kolb, C., Worsnop, D., Rudich, Y., DeCarlo, P., and Jimenez, J., "Particle Morphology and Density Characterization by Combined Mobility and Aerodynamic Diameter Measurements. Part 2: Application to Combustion-Generated Soot Aerosols as a Function of Fuel Equivalence Ratio," Aerosol Sci. And Tech., 38(12): 1206 (2004).

Nicolai, T., Durand, D., and Gimel, J., "Static Structure Factor of Dilute Solutions of Polydisperse Fractal Aggregates," Phys. Rev. B, 50(22): 16,357-16,363 (1994).

Park, K., Cao, F., Kittelson, D. B., and McMurry, P. H., "Relationship between Particle Mass and Mobility for Diesel Exhaust Particles," Environ. Sci. Technol., 37(3): 577-583 (2003).

Hull, P. Shepherd, I, and Hunt, A., "Modeling Light Scattering from Diesel Soot Particles," Appl. Opt., 43(17): 3433-3441 (2004).

Holve, D., "Real-Time Optical Smoke Meter (Size and Concentration) for Turbine Engines," Final Report, DOD AEDC PKP, FA9101-04-C-0027, May 18, 2007.

Lin, M.Y., Klein, R., Lindsay, H.M., Weitz, D.A., Ball, R.C., and Meakin, P., "The Structure of Fractal Colloidal Aggregates of Finite Extent," J. Colloid Interface Sci., 137: 263-280 (1990).

Dankers, S. and Leipertz, A., "Determination of primary particle size distributions from time-resolved laser-induced incandescence measurements," Applied Optics, 43(18): 3726-3731 (2004).

Whitefield, P., Hagen, D., and Lobo, P., "PM Characterization of Aircraft Engines," Project APEX, presented at 24th AAAR Conference, Austin, Texas, Oct. 20, 2005.

Kazakov, A and Frenklach, M., "Dynamic modeling of Soot Particle Coagulation and Aggregation: Implementation with the Method of Moments and Application to High-Pressure lamina Premixed Flames," Combustion and Flame 114:484-501 (1998).

Wang, G. and Sorensen, C., "Experimental test of the Rayleigh-Debye-Gans theory for light scattering by fractal aggregates," Applied Optics, 41(22): 4645-4651 (2002).

Park, Kittelson, and McMurry (Park, K., Kittelson, D., and McMurry, P., "A Closure Study of Aerosol Mass Concentration Measurements: Comparison of Values Obtained with Filters and by Direct Measurements of Mass Distributions," Atmospheric Environment 37: 1223-1230 (2003).

DeCarlo, P., Worsnop, D., Slowik, J., Davidovits, P., and Jimenez, J., "Particle Morphology and Density Characterization by Combined Mobility and Aerodynamic Diameter Measurements. Part 1, Theory," Aerosol Sci. and Tech., 38(12): 1185-1205 (2004).

Brown, W.K., and Wohletz, K. "Derivation of the Weibull Distribution Based on Physical Principles and its Connection to the Rosin-Rammler and Lognormal Distributions," Journal of Applied Physics, 78(4): 2758-2763 (1995).

Petzold, A and Schonlinner, M., "Multi-angle Absorption Photometry—A New Method for Measurement of Aerosol Light Absorption and Atmospheric Black Carbon," Journal of Aerosol Science, 35(4): 421-441 (2004).

Kreidenweis, S., "Effects of Mixing on Extinction by Carbonaceous Particles," Journal of Geophysical Research, 104 (D13): 1 5941-1 5954 (1999).

Zhu, J., Choi, M., Mulholland, G., and Gritzo, L, "Soot Scattering Measurements in the Visible and Near-infrared Spectrum," Proceedings of the Combustion Institute, vol. 28, p. 439-446, 2000.

Holve, D.J., "Real-time Soot Emissions Instrument for Gas Turbine and Diesel Engines," [Online] May 2007 Retrieved from the Internet: URL:http/www.processmetrix.com/STARMethod.pdf.

Litton, C.D., "Studies of the Measurement of Respirable Coal Dusts and Diesel Particulate Matter," Meas. Sci. Technol. 13:365-374 (2002).

Courteille, C. et al., "Particle Agglomeration Study in RF Silane Plamas: In Situ Study by Polarization-Sensitive Laser Light Scattering," J. Appl. Phys., 80(4): 2069-2078 (1996).

PCT international Search Report and the Written Opinion of the International Searching Authority, or the Declaration issued in related international application PCT/US2008/077412 (12 pages).

* cited by examiner

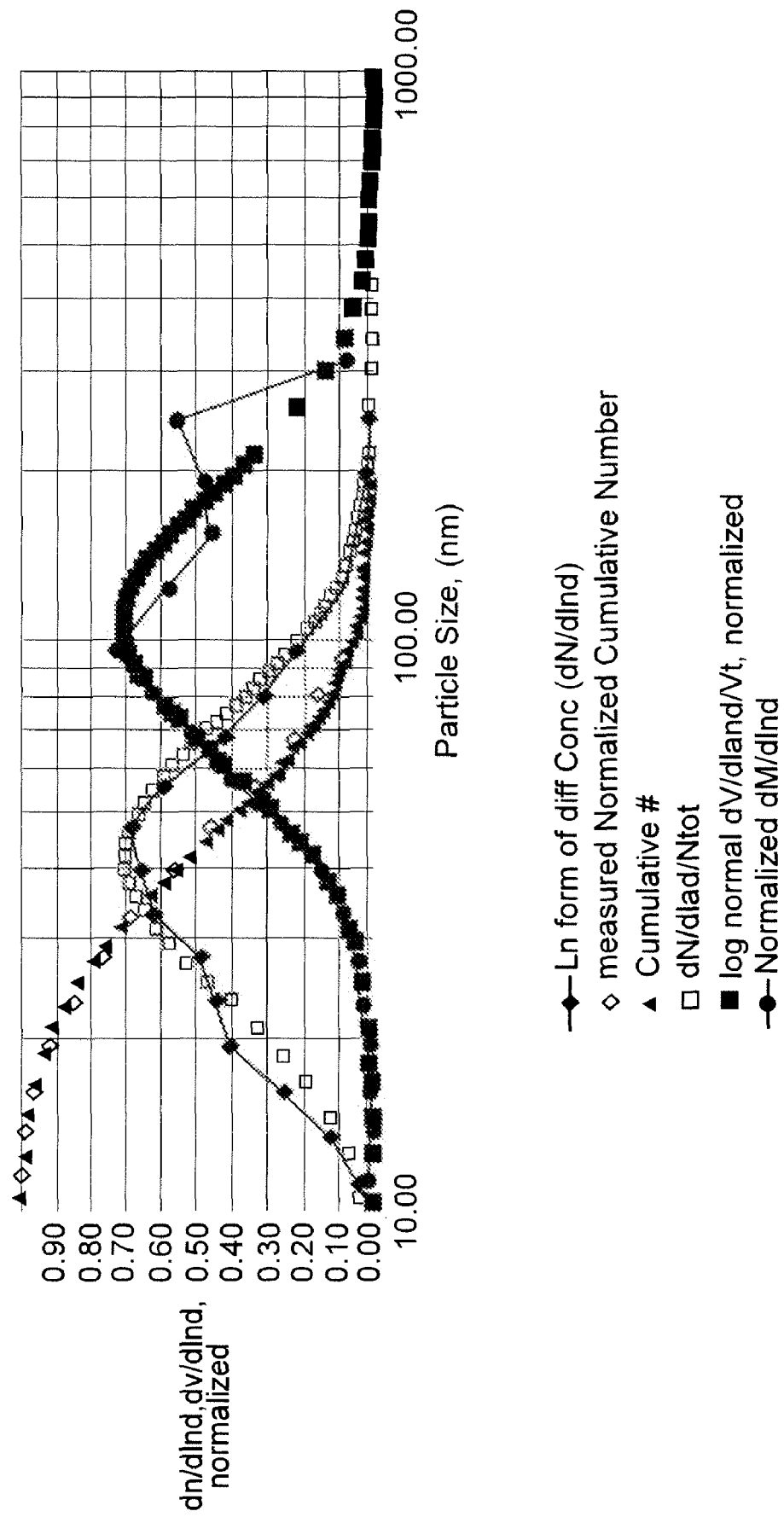
FIG. A1

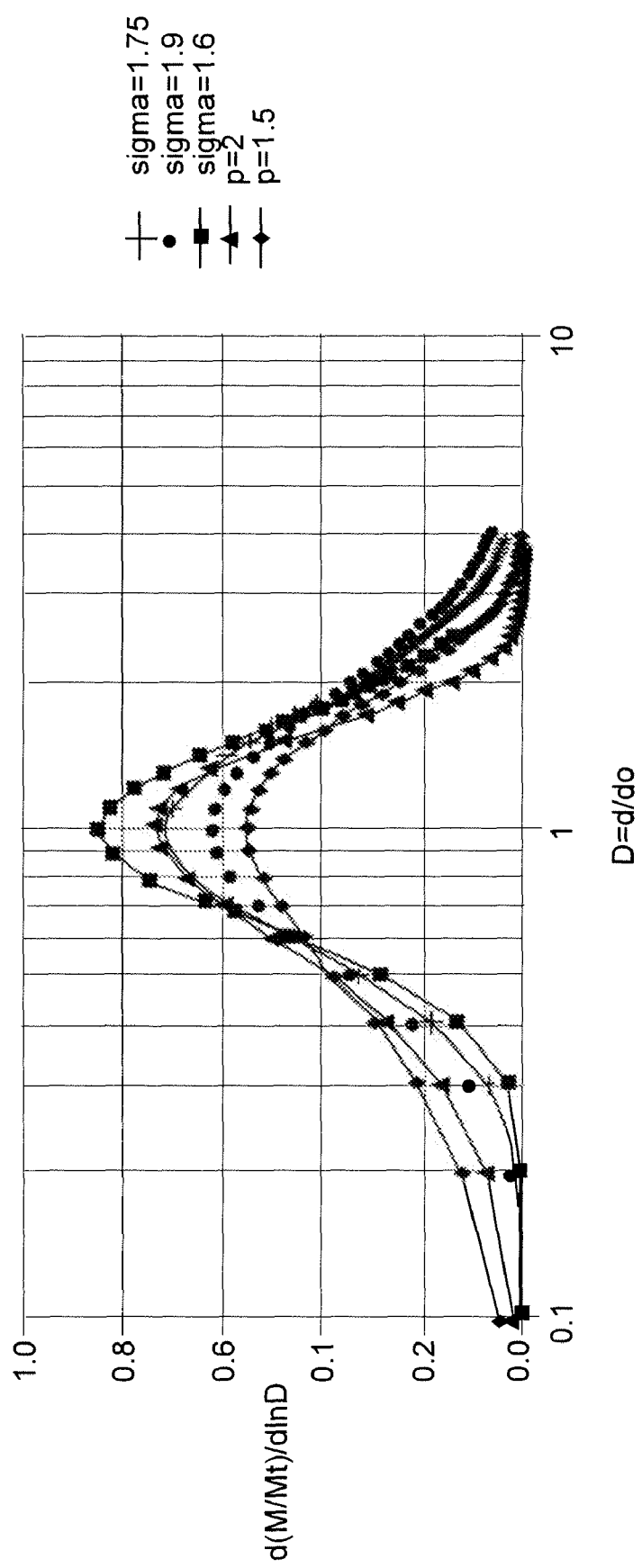
FIG. A2

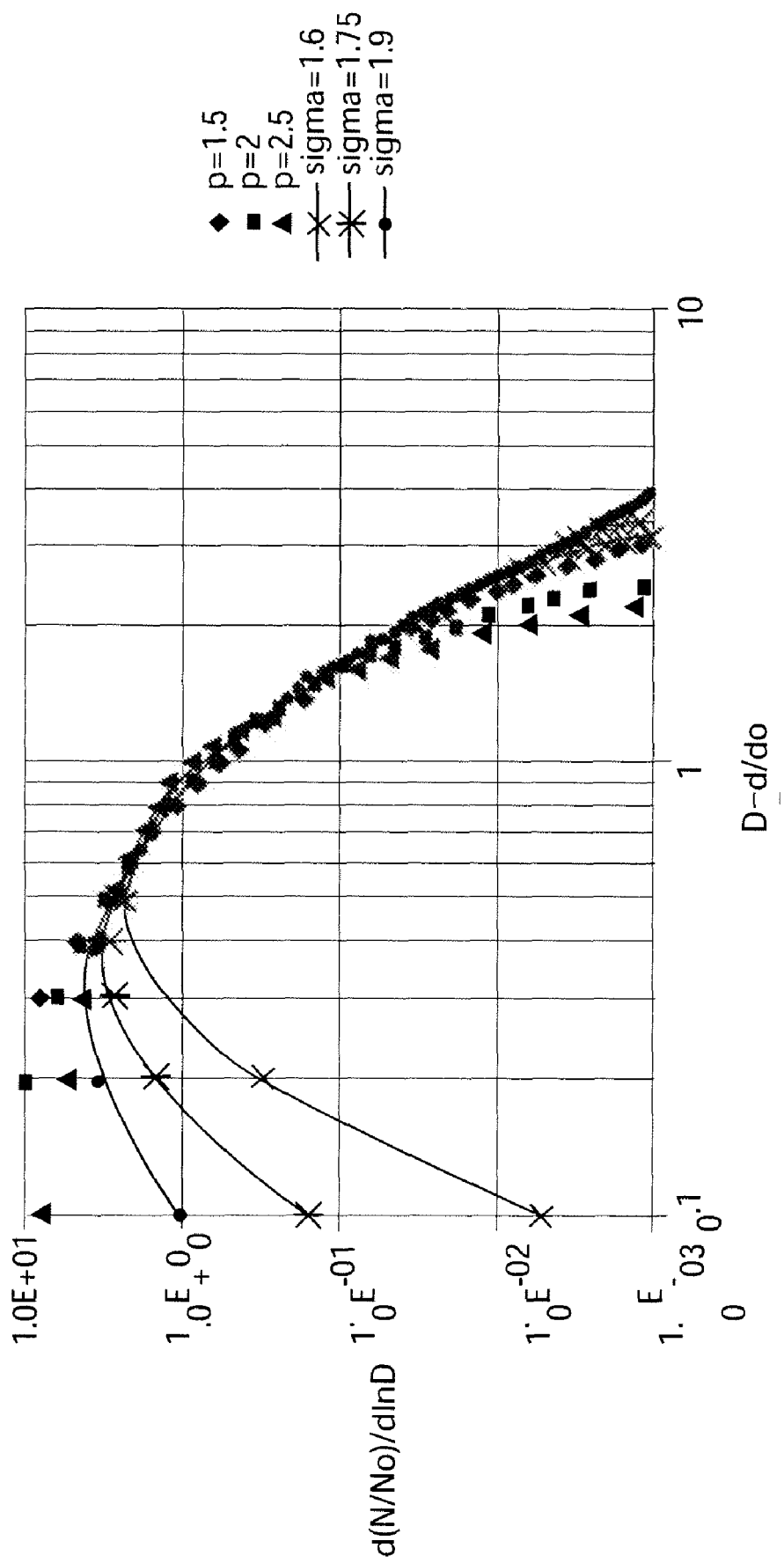
FIG. A3

# LASER-BASED APPARATUS AND METHOD FOR MEASURING AGGLOMERATE CONCENTRATION AND MEAN AGGLOMERATE SIZE

CROSS REFERENCE TO RELATED APPLICATIONS

This application claims priority to U.S. provisional patent application of Ser. No. 60/994,995, filed on Sep. 24, 2007, the contents of which are herein incorporated by reference in their entirety.

STATEMENT ABOUT FEDERALLY SPONSORED RESEARCH

At least part of the materials disclosed herein was made with Government support under Contract No. N68335-04-C-0007 (Navy) and FA9101-04-C-00 (Air Force). As such, the Government has certain rights therein as provided for by the terms of these contracts.

BACKGROUND OF THE INVENTION

1. Field of the Invention

The subject matter disclosed relates in general to the measurement of size and mass concentration of particles. More specifically, it relates to apparatuses and methods of making concentration and mean agglomerate particle size measurements using scattered light.

2. Description of the Related Art

The ability to measure and to quantify the behavior and characteristics of particles (e.g., measurement of individual size and local number and/or mass concentrations) is of utmost importance in a large number of applications of interest such as, for example, industrial boilers and furnaces, different processes in petroleum refineries, food preparation, and pollution of the environment caused by industrial and vehicular emissions. The need to perform particle-related measurement is further evidenced by the large number, and ever more stringent, governmental regulations dealing with the subject. One of the challenges in making these measurements relates to the fact that particle sizes ("small" or "large") and concentrations (dilute or dense flows) vary widely depending on the specific application. For example, during the combustion process inside a boiler or furnace one may be concerned with particle sizes varying from 1 mm down to 1 μm with concentrations ranging from 1 mg/m$^3$ to 50 g/m$^3$; however, when dealing with atmospheric pollution, the sizes of interest may be much smaller (e.g., ranging from 10 μm to 10 nm) and concentrations can be on the order of 1-1000 μg/m$^3$. Yet, in some other applications, the interest may be in even broader size distributions, as for example, particle sizes from 1 mm down to 1 nm. The technological challenge is how to make reliable measurements of this large size range under such a wide range of concentrations. There are many different instruments available to make measurement of particle size; however, laser-based techniques are the primary alternative for real-time measurement in dilute flows of very small particles and have provided the most reliable results. They typically include single-particle counters as well as ensemble instruments that measure multiple particle scattering. Examples include opacity, angular light diffraction, dynamic particle arrival fluctuations, and large-angle, phase-detected nephelometry. In general, the smaller the particle size and the more dilute the flow, the more difficult the measurement will be due to decreased scattering signals.

In laser-based ensemble instruments, a laser light source is provided and focused or collimated to form a probe volume and the light scattered, absorbed, and/or transmitted by the particles flowing through this probe volume is measured, using one or several light detectors. Light detectors are devices that produce a voltage or current signal that is related to the amount of light incident on the detector's face. Given the intermittent nature of the particles flowing in any system, detector signals naturally vary as a function of the particle number, size, and residence time in the probe volume.

As an example, classical nephelometry, or right angle scattering, measures the time-averaged scattering signal from a large number of particles (typically greater than 100 particles in a probe volume). For general types of particles in the size range of 0.2 to 1 micron, the scattering signal is roughly proportional to the particle concentration alone, while outside this range, the scattering signal becomes strongly dependent on both the particle size and concentration. In another example, opacity measurements determine the average amount of light that is absorbed and scattered out of a probe volume. For particles larger than 1-2 microns, this results in a simple relationship between the signal attenuation and the ratio of concentration to mean particle size. However, in both of these examples, a single scattering measurement does not provide independent information on both the particle size and concentration.

Another challenge in performing the above-summarized measurements and others is the fact that optical scattering properties are normally dependent on the type of particle being measured. For example, combustion soot has unique optical scattering properties. Many optical measurement techniques have been developed over the years that measure light scattering at one or more angles, or use absorption methods to determine the mass concentration of particles, as for example, black carbon soot. The decreasing concentration levels occurring in practical combustion engines limit absorption methods. Light scattering methods have invariably required the use of empirical calibrations to relate the scattering measurement to the desired mass concentration or particle size. Solution of the light-scattering equations in conventional two-angle scattering measurements provided by De Luliis et al. (De Luliis, S., Cignoli, F., Benecchi, Zizak, G. "Determination of Soot Parameters by a Two-angle Scattering-extinction Technique in an Ethylene Diffusion Flame," Applied Optics, 37(33): 7865-7874 (1998), the contents of which are herein incorporated by reference in their entirety) are based on the explicit dependence of particle light scattering properties on geometrical properties of the particle structure.

Therefore, it is desirable to have an optical instrument to quantitatively measure the mass concentration and mean particle size using light scattering measurements to give fundamental size and concentration measurements in a way that is based on fundamental theory without empirical calibration so as to provide a formulation that gives a direct and straightforward interpretation of the size and concentration in terms of the measured scattering signals, the instrument properties, and the particle optical properties. As used hereinafter, the expression "particles" refers to any agglomerates made up of similarly sized primary particles, such as, for example, soot.

BRIEF SUMMARY OF THE INVENTION

One or more of the above-summarized needs or others known in the art are addressed by apparatuses configured to measure average size and concentration of a polydispersed agglomerate that include a light source, a first light detector positioned at a first angular position, $\theta_1$ from the direction of the beam of light, and a second light detector positioned at a second angular position, $\theta_2$, such that an average concentration of the polydispersed agglomerate, $C_m$, per unit total scattered light, $P_{T\theta}$, is given by:

$$\frac{C_m}{P_{T\theta}} = f_1 f_2 C_m \#,$$

where $f_1$ is a function of primary particle optical properties, $f_2$ is a function of a configuration of the apparatus, and $C_m\#$ is a nearly invariant function of a scattering ratio, $R_{\theta 1/\theta 2}$, of the scattered light measured by the first and the second light detectors.

Apparatuses for measuring average size and concentration of a polydispersed agglomerate of primary particles are also included in the scope of the subject matter disclosed. Such apparatuses include a first light source configured to emit a first beam of light having a first wave length in a first direction; a second light source configured to emit a second beam of light having a second wave length in a second direction, the second wave length being different than the first wave length; and a light detector configured to generate a first signal proportional to light scattered from the first light source by the polydispersed agglomerate and to generate a second signal proportional to light scattered from the second light source by the polydispersed agglomerate, wherein an average concentration of the polydispersed agglomerate, $C_m$, per unit total scattered light, $P_{T\theta}$, is given by:

$$\frac{C_m}{P_{T\theta}} = g_1 g_2 C_m \#,$$

where $g_1$ is a function of optical properties of the primary particles, $g_2$ is a function of a configuration of the apparatus, and $C_m\#$ is a nearly invariant first function of a scattering ratio, $R_{\lambda 1/\lambda 2}$, of the first signal to the second signal.

Apparatuses for measuring an average mass concentration of a polydispersed agglomerate of primary particles are also included in the scope of the subject matter disclosed, such apparatuses including a light source configured to emit a beam of light in a first direction, the beam of light having a wave length in the ultraviolet to blue range; and a light detector configured to generate a signal proportional to light scattered from the light source onto the light detector by the polydispersed agglomerate, wherein an average mass concentration of the polydispersed agglomerate, $C_m$, per unit total scattered light, $P_{T\theta}$, is given by:

$$\frac{C_m}{P_{T\theta}} = f_1 f_2 C_m \#,$$

where $f_1$ is a function of optical properties of the primary particles, $f_2$ is a function of a configuration of the apparatus, and $C_m\#$ is substantially constant.

Methods of measuring average size and concentration of a polydispersed agglomerate are also within the scope of the subject matter disclosed herein, these methods including the steps of emitting a beam of light from a light source, measuring light scattered from the polydispersed agglomerate passing through a probe volume formed in the beam of light with a first light detector positioned at a first angular position, $\theta_1$, from the direction of the beam of light, measuring light scattered from the polydispersed agglomerate passing through the probe volume with a second light detector positioned at a second angular position, $\theta_2$, from the direction of the beam of light, and calculating an average concentration of the polydispersed agglomerate, $C_m$, per unit total scattered light, $P_{T\theta}$, using the following equation:

$$\frac{C_m}{P_{T\theta}} = f_1 f_2 C_m \#,$$

where $f_1$ is a function of primary particle optical properties, $f_2$ is a function of a configuration of the apparatus, and $C_m\#$ is a nearly invariant first function of a ratio, $R_{\theta 1/\theta 2}$, of the scattered light measured by the first light detector to the scattered light measured by the second detector.

The above brief description sets forth features of the various embodiments of the present invention in order that the detailed description that follows may be better understood, and in order that the present contributions to the art may be better appreciated. There are, of course, other features of the invention that will be described hereinafter and which will be for the subject matter of the appended claims.

In this respect, before explaining several embodiments of the invention in detail, it is understood that the various embodiments of the invention are not limited in their application to the details of the construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which the disclosure is based, may readily be utilized as a basis for designing other structures, methods, and/or systems for carrying out the several purposes of the present invention. It is important, therefore, that the claims be regarded as including such equivalent constructions insofar as they do not depart from the spirit and scope of the present invention.

Further, the purpose of the foregoing Abstract is to enable a patent examiner and/or the public generally, and especially scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

BRIEF DESCRIPTION OF THE SEVERAL VIEWS OF THE DRAWINGS

In order to facilitate the understanding of the various disclosed embodiments, their description and associated explanation will be provided with reference to the specific exemplary embodiments illustrated in the appended drawings or figures (not drawn to scale), wherein.

FIG. A1 illustrates a typical gas turbine number and volume size distributions measured by SMPS;

FIG. A2 illustrates a linear scaling comparison of mass frequencies for log normal and Rosin Rammler distribution functions using several values of the distribution width parameters for each distribution; and FIG. A3 illustrates a log scaling comparison of number frequencies for lognormal and Rosin Rammler distribution functions using several values of the distribution width parameters for each distribution.

DETAILED DESCRIPTION OF THE INVENTION

Figure 1:
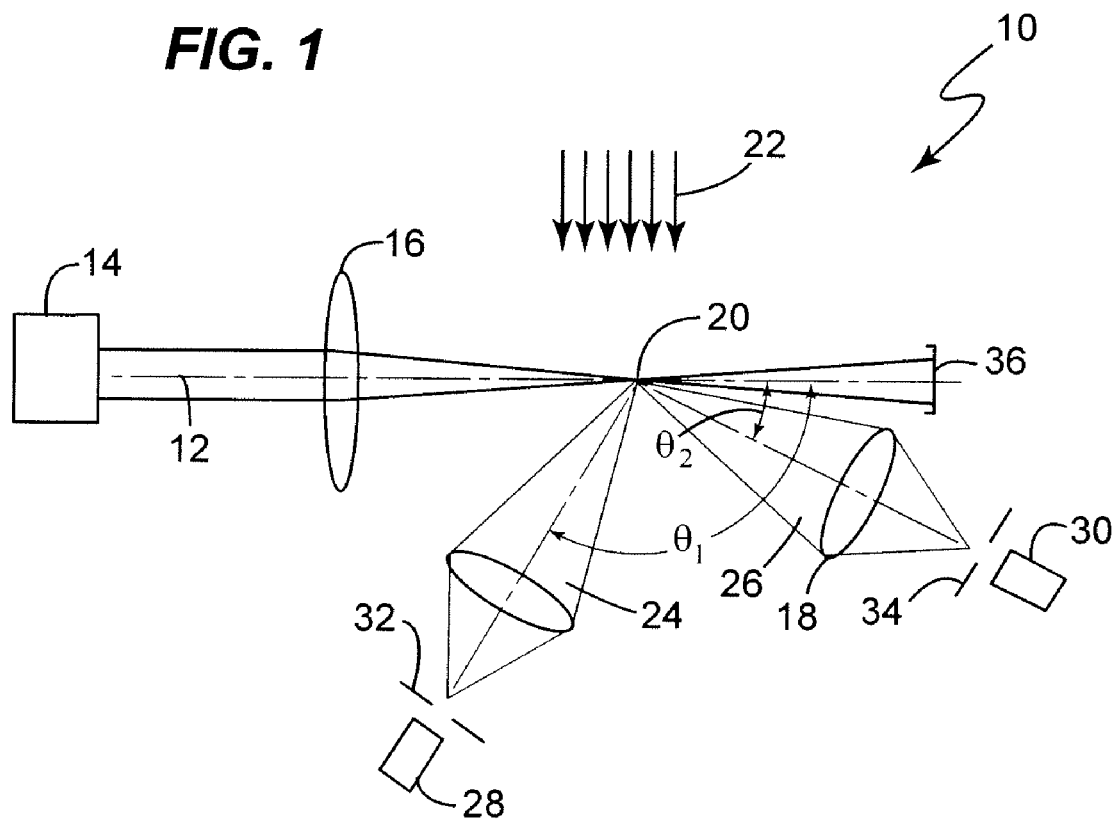
FIG. 1 illustrates a schematic diagram of a light scattering and detection geometry for scattering at two angles according to an embodiment of the subject matter disclosed.
Figure 2:
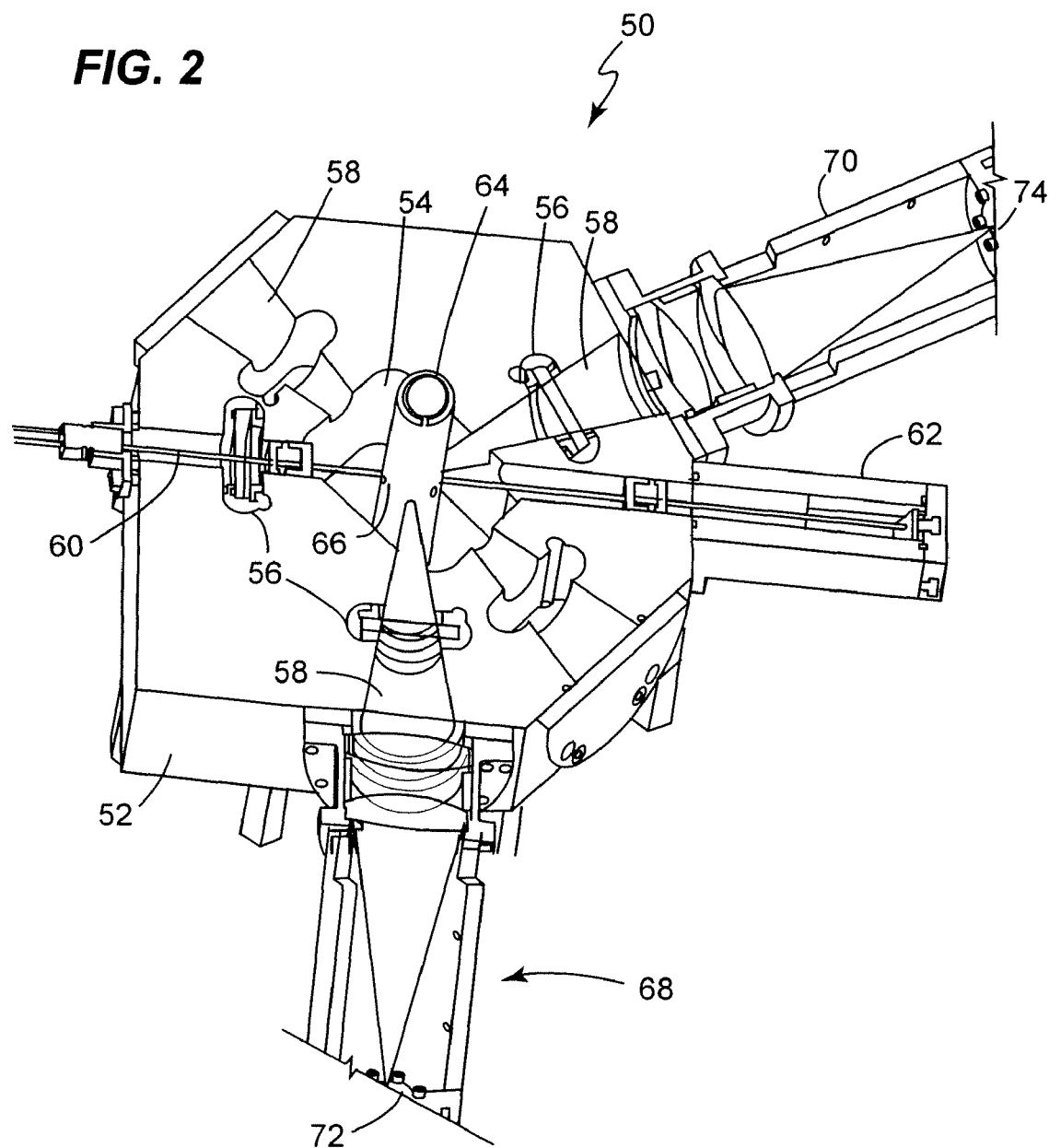
FIG. 2 illustrates an exemplary embodiment of an apparatus to measure concentration and mean agglomerate size using the light scattering and detection geometry shown in FIG. 1 for flow samples that are transported to the apparatus by an extractive sample line.
Figure 3:
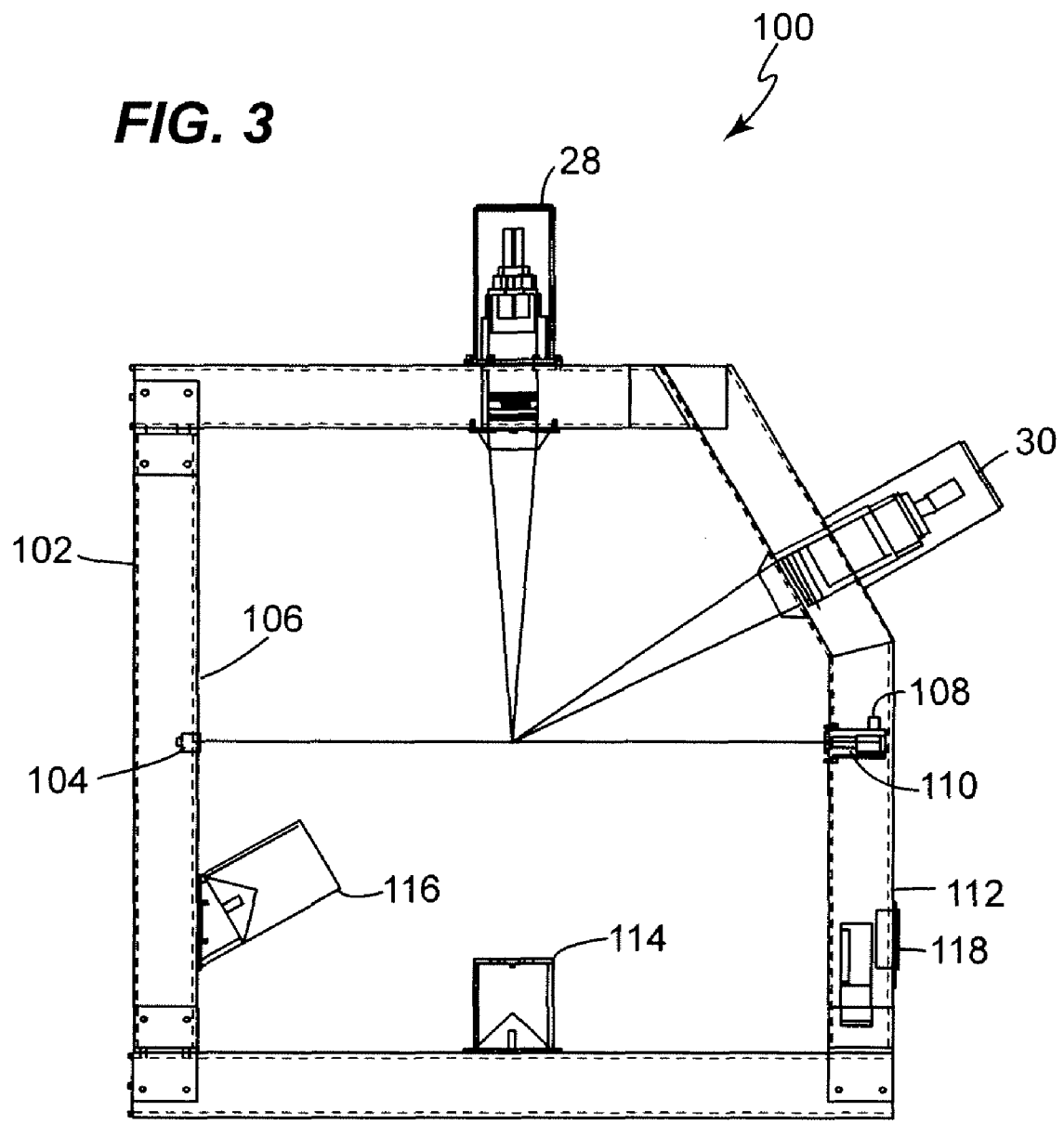
FIG. 3 illustrates another exemplary embodiment of an apparatus for in-situ measurements of a flow (without sample transport) to measure concentration and mean agglomerate size using the light scattering and detection geometry shown in FIG. 1.

FIG. 1 illustrates a schematic diagram of a light scattering and detection geometry for scattering at two angles ratio according to an exemplary embodiment of the subject matter disclosed. FIGS. 2 and 3 illustrate embodiments of apparatuses to measure concentration and mean agglomerate size of an extracted sample or in-situ, respectively, using the light scattering and detection geometry shown in FIG. 1. In FIG. 1, a light scattering and detection geometry 10 for Scattering at Two Angles Ratio (hereinafter STAR) is disclosed in which the light 12 of a light source 14 is collimated or focused by a first focusing lens 16 creating, together with a second focusing lens 18, a probe volume 20. Although lens are illustrated in FIG. 1 to focus and/or collect scattered light, it should be understood that any light collecting device, including, but not being limited to, an elliptical mirror, may be used for the purpose of defining the probe volume 20, focusing the light from the light source 14, and collecting the scattered light generated by the particles in the particle flow indicated in FIG. 1 by the arrows 22. One of the advantageous features of this invention is the measurement of the mean agglomerate size and the mass concentration of the particles contained in the particle flow 22 flowing through the probe volume 20.

Normally, the particle flow 22 is composed of particles of different sizes, i.e., size classes, having different concentration levels, i.e., number of particles per unit volume. The light scattered by the particle flow 22 as it passes through the probe volume 20, identified in FIG. 1 as elements 24 and 26, is detected by at least two light detectors 28 and 30, which create voltage and/or current signals that are proportional to the product of the number of particles and their respective scattering intensity. Non-limiting examples of the light detectors 28 and 30 include, but are not limited to, a photomultiplier tube, a Silicon diode, or an avalanche photodiode. Although the voltage and/or current signals from the light detectors 28 or 30 generally vary with time depending on the size of the particles, their location in the probe volume, and the number of particles in the sample volume, these signals are generally averaged over time and give an average DC signal output. (For a given particle, the intensity varies with the location of the particle in the probe volume because the intensity of the light source is normally not uniform along a cross-section of the light beam.) The determination of the mean agglomerate particle size and concentration of the particles in the particle flow 22 is based on the average or DC components of the two detectors. A more detailed explanation of this procedure is provided below. Slits 32 and 34 may be disposed in front of each light detector 28 and 30 to control the amount of light incident thereon and to minimize exposure to stray light from the laser or background sources of light. In addition, as also illustrated in FIG. 1, the light scattering and detection geometry 10 may also include a beam dump 36 which measures the laser power in a way that minimizes backscattered stray laser light. Measurement of the laser beam power corrects for variations in laser power, which directly scale the measured scattering signals at the two detectors.

In the exemplary embodiment shown in FIG. 1 (not drawn to scale) the first light detector 28 is located at a first angular position, $\theta_1$, of approximately 90° with respect to the forward direction of the light 12 emitted from the light source 14 and the second light detector is located at a second angular position, $\theta_2$, of approximately 30° from the forward direction of the light 12. It should be noted however that the particular angular positions of the first light detector 28 and the second light detector 30 are not limited by the illustration of FIG. 1. Other detector angular positions can range from 0 to 180 degrees for the first light detector 28 (or the large-angle detector) and from 0 to 180 degrees from the second light detector 30 (or the small-angle detector), the angular position for the first light detector 28 being always larger than the angular position for the second light detector 30. It should be noted here, as understood by those of ordinary skill in the applicable arts, that for given first and second angular positions for the first and second light detectors 28 and 30, those components of the light scattering and detection geometry 10 do not necessarily have both to be on the same plane as shown in the exemplary embodiment of FIG. 1. In fact, for a given first and second angular positions $\theta_1$ and $\theta_2$, the first and second detectors 28 and 30 may be disposed in any azimuthal position around the light beam.

As noted previously, the light scattering and detection system illustrated in FIG. 1 can be implemented in a small package sampling instrument, as shown in FIG. 2, to which a sample extracted from the flow in which the size and concentration of the particles are being measured (hereinafter extractive-STAR or ex-STAR 50) or as a non-intrusive instrument without sample transport and with optics placed external to the particle flow, as shown in FIG. 3, for in-situ measurements (hereinafter in-situ STAR or in-STAR 100). As it will be further explained below, STAR instruments are capable of making real-time measurements (using, for example, sampling rates of 10 Hz or higher) of soot mass concentration: (0.001-1000 mg/m$^3$), average volume agglomerate diameter: (60-500 nm), number and surface area of primary particles in agglomerates, and Smoke number (reflectance). Any sampling frequency for real-time measurements may be selected according to the application and characteristics of data acquisition systems being used, thus the above-noted range may be favored, but should not be considered as a limitation.

STAR instruments and related methods measure light scattering signals at two different angles to determine the volume mean soot agglomerate diameter and mass concentration. These real-time optical instruments have been demonstrated for use in many industrial devices, including, but not limited to, gas turbine and diesel engines, using extracted samples (from an exhaust stream or diluted exhaust samples in conformance with regulatory requirements) or in-situ measurements. However, those of ordinary skill in the applicable arts will appreciate that several other industrial applications may benefit from the subject matter disclosed herein, including, but not being limited to, industrial boilers, gasoline engines, or any other non-vehicle applications, such as, for example, locomotives, off-highway vehicles (such as articulated trucks, backhoe loaders, cold planers, compactors, feller bunchers, forest machines, forwarders, harvesters, hydraulic excavators, industrial loaders, knuckleboom loaders, material handlers, motor graders, multi-terrain loaders, off-highway tractors, off-highway trucks, paving equipment, pipe layers, road reclaimers, scrapers, skid-steer loaders, skidders, telehandlers, track loaders, track-type tractors, underground mining, wheel dozers, wheel excavators, and wheel loaders), marine applications, and cranes, to name only a few examples. Interpretation of the scattering measurements is based on a new analysis of light scattering theory that describes the agglomerate (e.g., black carbon soot) as fractal agglomerates of well-defined spherical primary particles. One of the advantageous features of the disclosed apparatuses and methods is the fact that three optical scattering properties of the agglomerate can be combined into one overall property constant, that is nearly invariant for a variety of substances in a given application of interest (e.g., fuel and combustor conditions, respectively). In engine exhaust applications, STAR has capabilities for measurement of mass concentration and agglomerate size over six orders of magnitude, allowing direct exhaust measurements, is quantitative at 1 µg/m$^3$, and is suitable for measurements following a Diesel Particulate Filter (DPF) with air dilution. Results are obtained quickly, and can readily follow engine transients at typical frequencies, including, but not being limited to, 10 Hz. Accuracy is comparable to that of Method 5 filter measurements (which typically ignore sample line losses), and precision is better than 4%.

As it will be further disclosed below, the two instrument embodiments (ex-STAR, which is based on extractive sampling of the particle flow and in-STAR, which is an in-situ configuration that can measure exhaust flows) have been calibrated, tested, and validated on a variety of industrial applications, including, but not limited to, diesel and gas turbine engines. In addition, as already noted, other industrial applications, such as, but not limited to, industrial boilers, gasoline engines, or any other non-vehicle applications will benefit of the subject matter disclosed herein. Optical parameters found in the open literature (without resorting to arbitrary calibrations) are used to predict values of the mass concentration and Smoke Number (SN) that are in good agreement with independent filter measurements. It has also been shown that one can relate the SN to the mass concentration, although there is an additional dependence on the SN filter, face velocity, and particle size.

FIG. 2 illustrates a cutaway drawing of an exemplary embodiment of the ex-STAR 50 device. As shown, the instrument includes a central body 52 that incorporates a central opening, or flow cell 54, several removable cartridge windows 56, and a plurality of light passages 58. In operation, a laser beam 60 passes through one of the removable cartridge windows 56, through one of the light passages 58, through the flow cell 54, through another light passage 58, and into a beam detector/dump 62. As also shown, in the flow cell 54, a sampling tube 64 is used to bring the flow of particles to be measured to the flow cell 54. The sampling tube 64 includes several orifices 66 for the passage of the laser beam 60 and also for the collection of scattered light by a first lens/receiver 68 and a second lens/receiver 70, having respectively a first light detector 72 and a second light detector 74 disposed at respective end portions thereof. Light scattered by the particles flowing through the sampling tube 64 is collected by each of the first and second lens/receivers 68 and 70 and focused into their respective first and second light detectors 72 and 74. This optical configuration of the ex-STAR 50 together with its associated electronics are disposed within a protective enclosure (not shown) with flow, temperature, and pressure controls to control the extracted sample flow as well as other flow rates, such as that of a purge gas to keep optical elements clean.

In the in-STAR 100 embodiment, as shown in FIG. 3, the system components, including the first light detector 30 and the second light detector 28, are mounted to a frame 102 so that the instrument may be mounted around the particle flow to be measured, such as for example, but not as a limitation, the exhaust of an aircraft engine. As shown, the frame 102 includes a plurality members connected to each other so as to define a central opening for the particle flow 22 (not shown in FIG. 3, but normally flowing in a direction perpendicular to the view shown). A light source 104 is also mounted to a first member 106 of the frame 102 and a beam power diode 108 and beam dump 110 are disposed opposite to the light source 104 on a second member 112 of the frame 102. Back light dumps 114 and 116 may also be provided for the first and second light detectors 30 and 28, respectively, so as to minimize measurement disturbances by stray light. All components of the in-STAR system 100 are connected to an external control device (not shown) at a connection panel 118 by known methods.

As it will be appreciated by those of ordinary skill in the applicable arts, after evaluation of the subject matters disclosed herein, embodiments of the in-STAR 100 and/or ex-STAR 50 instruments may be used in many different applications, including, but not being limited to, industrial boilers, gasoline and diesel engines in automobiles, gas turbine engines used in aircraft propulsion or power generation, or any other non-vehicle applications, such as, for example, locomotives, off-highway vehicles (such as all types of earth-moving heavy equipment, as noted hereinabove), marine applications, and cranes, to name only a few examples.

Typically, the size distribution of particles in the particle flow can be represented by a mathematical expression having two adjustable parameters, namely a mean particle size and an effective distribution width. Having such a mathematical expression and assuming that the particle arrival rates in the probe sample volume are Poisson-distributed, i.e., every particle size has an equal chance of being located at any point within the sample volume, a relationship exists between particle number in the probe volume and the measured DC components of the two detectors. This relationship is described in quantitative detail further below.

Several equivalent forms of two-parameter mathematical distributions may be used in a theoretical analysis to compute values of $C_m$ (mean agglomerate concentration) and $d_{go}$ (mean agglomerate size) that vary less than ±7%, depending on the range of typically measured distribution widths. The following outlines the development of the scattering theory for the implementation of the various embodiments of the subject matter disclosed, beginning with the simple case of a monodisperse particle distribution, and then followed by the general case of a two-parameter agglomerate size distribution. It should be noted that the measurements and predicted results made by the instant invention are based on fundamental scattering theory, with no adjustable parameters, and applicable to any agglomeration of similarly sized particles, as, for example, soot particles.

1.0 Development of Theory for Star

The basic theory using particle fractal aggregate (PFA) and Rayleigh-Debye-Gans (RDG) scattering has been developed previously by numerous authors and the fundamentals have been summarized in a review paper by Sorensen (Sorensen, C. M., "Light Scattering by Fractal Aggregates: A Review", Aerosol Sci. and Tech. 35: 648-687 (2001), incorporated herein by reference in its entirety). In another paper (De Luliis et al., supra), the basic two-angle ratio method has been described and experimental measurements exist with results that are consistent therewith. However, the analyses used provide implicit solutions, so that it is unclear as to the explicit relationship (and connection) between all measurement parameters. In the analysis described below, the inventor has developed an explicit relationship for the mass concentration and mean particle sizes, which are directly related to particle optical and physical properties, instrument parameters, and a nearly invariant function, which is defined hereinafter as the dimensionless quantity $C_m\#$ that is dependent only on the measured scattering signal at two angles. As used herein throughout, the expression "a nearly invariant function" refers to any mathematical curve fit, including, but not being limited to, a polynomial or numerical curve fit, to name just a few, using typical ranges of particle fractal dimension and other soot properties, having an average deviation of less than ±10% from the mean fitted function. One of the advantages of this approach is that one can combine all the particle properties into a single product function, which is nearly invariant itself. Experimental results of soot measurements for combustion applications show that one can use standard literature values for soot properties, and can obtain good agreement with independent filter measurements of mass concentration. The following sections further explain the subject matter disclosed as applied to soot measurements. However, those of ordinary skill in the application arts will appreciate that the approach can be extended to other particle agglomerates which are also within the scope of the various embodiments of the disclosed inventions.

1.1 Primary Particles and Soot Agglomerates

Primary particles, with uniform and reasonably well-defined diameter, $d_p$, and density, $\rho_p$, are the building blocks of soot agglomerates. The mass of a primary particle, $m_p$, and its surface area, $A_p$, (assuming that contact area is negligible) are given by $(\pi/6)\rho_p d_p^3$ and $\pi d_p^2$. It is known that $d_p$ is approximately constant (25-35 nm) for a wide range of combustion conditions, including a variety of flames, engines, and fuels (see, for example, Neer, A., and Koylu, U., "Effect of Operating Conditions on the Size, morphology, and concentration of Submicrometer Particulates Emitted from a Diesel Engine" Combustion and Flame, 146: 142-154 (2006); and Hu, B., and Koylu, U., "Size and Morphology of Soot Particulates Sampled from a Turbulent Nonpremixed Acetylene Flame", Aerosol Science and Technology, 38: 1009-1018 (2004), both incorporated herein by reference in their entirety).

Figure 4:
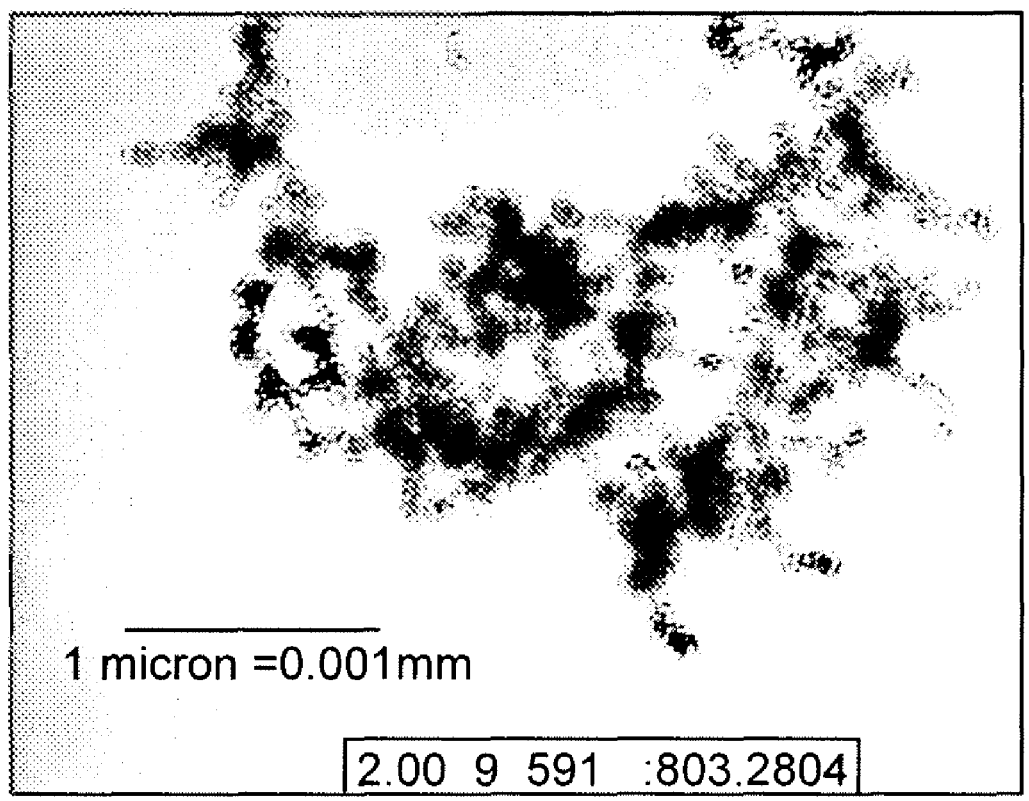
FIG. 4 illustrates a transmission electron micrographic photograph of a large fractal soot agglomerate built from mono-disperse primary particles.

Fractal aggregates are assembled from primary particles using Particle Fractal Aggregate, or PFA, theory. The number, n, of primary particles in a fractal aggregate of diameter $d_g$ (based on radius of gyration) is given by:

$$n = k_o (d_g/d_p)^{D_f}. \tag{1}$$

where $D_f$ is the fractal dimension measured in a variety of flames and engines (see, for example, Neer and Koylu and Hu and Koylu, supra). The radius of gyration is the natural optical size descriptor of soot agglomerates and is used to characterize the optical structure function. The gyration diameter can be measured experimentally by using Transmission Electron Micrography (TEM), as shown in FIG. 4. FIG. 4 is a transmission electron micrographic photograph of a large fractal soot agglomerate built from "mono-disperse" primary particles. Those of ordinary skill in the applicable arts will appreciate that a more typical agglomerate size is shown in that figure in the lower right-hand corner. FIG. 4 also illustrates the transparent nature of the non-overlaid particles.

While there is reasonable consensus on measured fractal dimensions and even the soot properties can be reasonably defined, there has been a factor of two variation in literature values for the constant $k_o$, which is important for obtaining accurate mass measurements (see, for example, Hu and Koylu, supra; and Koylu, U. O., Faeth, G. M., Farias, T. L., and Carvalho, M. G., "Fractal and Projected Structure Properties of Soot Aggregates," Combustion and Flame 100: 621-633 (1995), which is incorporate herein by reference in its entirety). There is general agreement that the fractal dimension is in the range of 1.7-1.9, and a mean value of $D_f=1.8$ is used herein. The question is what value of $k_o$, to use for the large particle limit, given that literature values range over a factor of two, from 1.3 by Sorensen and co-workers in several papers (determined primarily by Monte-Carlo simulations of diffusion-limited cluster-cluster agglomeration and light scattering measurements) to $k_o=1.7$-$2.6$ determined by TEM measurements of diesel soot gyration diameters and light scattering measurements (see, for example, Hu and Koylu and Koylu et al, supra; and Sorensen, C. and Feke, G. "The Morphology of Macroscopic Soot," Aerosol Sci. and Technology, 25: 328-327 (1996), which is incorporated herein by reference in its entirety).

All sets of results appear to be internally consistent, but this range of uncertainty is large given the better than 5% precision of optical measurements. A paper by Brasil, et al. (Brasil, A. M., Farias, T. L., and Carvalho, M. G., "Evaluation of the Fractal Properties of Cluster-Cluster Aggregates," Aerosol Science and Technology 33: 440-454 (2000), which is incorporated herein by reference in its entirety) confirms that Monte-Carlo simulations for $D_f$ and $k_o$ are consistent with results by Sorensen, supra, but they also show that most experimental measurements for $k_o$ are significantly higher. They propose a mechanism due to sintering, which increases the contact area between primary particles and gives similar fractal dimensions (simulation calculations), but also generates increased values of $k_o$ by a factor of two, closer in agreement to physical measurements of $k_o$. In a recent paper by Hu, et al. (Hu, B., Yang, B., and Koylu, U., "Soot Measurements at the Axis of an Ethylene/air Non-premixed Turbulent Jet Flame," Combustion and Flame, 134: 93-106 (2003), incorporated herein by reference in its entirety), they obtained values of $D_f=1.74\pm0.11$ and $k_o=2.2\pm0.4$ for a turbulent propane flame, along with $d_p \approx 25$-$35$ nm at longer reaction times. Similarly, Neer and Koylu, supra, obtained values of $D_f=1.77\pm0.14$ and $k_o=1.9\pm0.5$ for a diesel engine operating over a range of load and RPM conditions, along with $d_p \approx 25$-$35$ nm. All these values are consistent with other research measurements referred by Neer and Koylu, supra. No equivalent results have been obtained for gas turbines, although mobility measurements of soot size distributions in gas turbines show similar behavior to diesel engines (see, for example, Slowik, J., Stainken, K., Davidovits, P., Williams, L., Jayne, J., Kolb, C., Worsnop, D., Rudich, Y., DeCarlo, P., and Jimenez, J., "Particle Morphology and Density Characterization by Combined Mobility and Aerodynamic Diameter Measurements. Part 2: Application to Combustion-Generated Soot Aerosols as a Function of Fuel Equivalence Ratio," Aerosol Sci. and Tech., 38(12): 1206 (2004), incorporated herein by reference in its entirety).

This uncertainty is resolved herein by reference to a previously developed analysis by Nicolai, et al. (Nicolai, T., Durand, D., and Gimel, J., "Static Structure Factor of Dilute Solutions of Polydisperse Fractal Aggregates," Phys. Rev. B, 50(22): 16,357-16,363 (1994), incorporated herein by reference in its entirety), who showed that the theoretical value $k_o$ is consistent with this inventor's measurements and other recent measurements (see, for example, Neer and Koylu, supra). The analysis of Nicolai et al., supra, will be discussed further below. However, first the PFA theory is confirmed to be consistent with experimental measurements, and then the general relationship for mass concentration as a function of the light scattering parameters is derived herein below.

Given the fractal nature of soot, it is important to note that the aggregate particle density varies with aggregate diameter. Indeed, aggregate particle densities in diesel engines, based on the mobility diameter, have been measured, and can be used as another test of the validity of the PFA theory defined above. This is a significant relationship, and it will be shown herein below that both the mass and scattering decrease with increasing aggregate size, compared to the normal assumption of uniform-density, hard-sphere particles.

The aggregate density, based on the gyration diameter ($\approx$mobility diameter up to 300-400 nm) can be derived as:

$$\rho_g = n m_p / (\pi/6) d_g^3, \text{ where } m_p = (\pi/6) \rho_p d_p^3. \quad (2)$$

Using the relationships for n from Equation (1), one obtains:

$$\text{for } (d_g/d_p) < 3 \text{ and } D_f = 2.4, \rho_g/\rho_p = (d_g/d_p)^{-0.6}, \text{ and} \quad (3)$$

$$\text{For } (d_g/d_p) > 3 \text{ and } D_f = 1.8, \rho_g/\rho_p = k_o (d_g/d_p)^{-1.2}. \quad (4)$$

Figure 5:
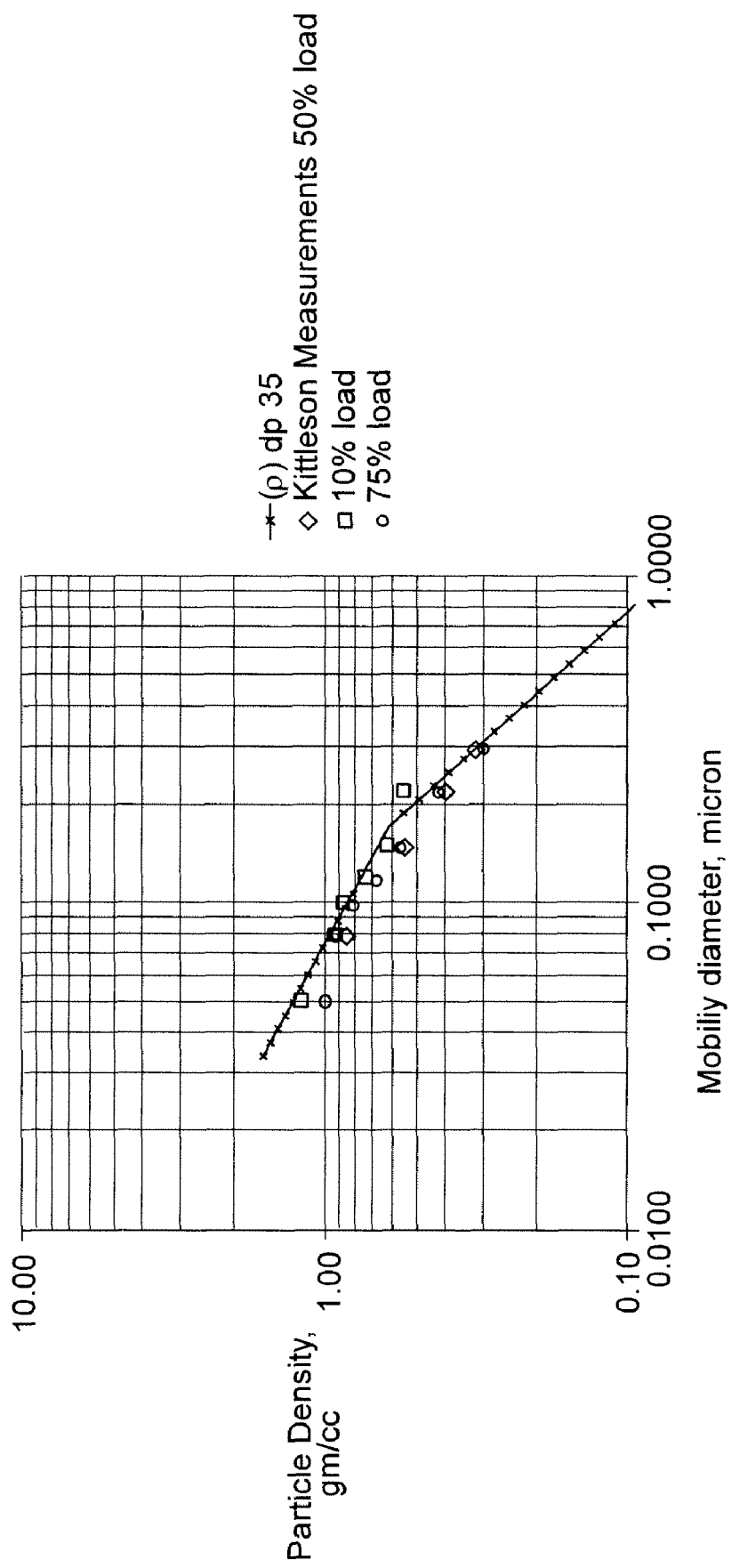
FIG. 5 illustrates measured values of particle density as a function of mobility diameter from a diesel engine at various loads compared with prediction of same using Particle Fractal Aggregate theory with $d_p=35$ nm, $\rho_p=1.7$ gm/cm$^3$, $k_o=1.9$ and $d_g=d_p$.

Verification of PFA theory can be obtained by comparing these formulae with experimental measurements (see, for example, Park, K., Cao, F., Kittelson, D. B., and McMurry, P. H., "Relationship between Particle Mass and Mobility for Diesel Exhaust Particles," Environ. Sci. Technol., 37(3): 577-583 (2003), incorporated herein by reference in its entirety) as shown in FIG. 5. FIG. 5 shows measured values of particle density as a function of mobility diameter from a diesel engine at various loads, compared with prediction of same using PFA theory with $d_p=35$ nm, $\rho_p=1.7$ gm/cm$^3$, $k_o=1.9$ and $d_g=d_p$, which are also used for the scattering analysis disclosed here. The comparison with the data of Park et al., supra, is good over the entire range of practical diameters measured in all of the diesel experiments disclosed herein which range from 100 to 400 nm. These results alone confirm that the PFA theory is accurate and that the optical constants $k_o=1.9$, and $D_f=1.8$, derived from independent measurements, are consistent.

Although diesel combustion appears to be quite different from gas turbine combustion, the temperatures, pressures, and residence times for combustion are not that dissimilar. Also one should note that many of the fundamental PFA parameters, e.g. fractal dimension and primary particle size, have been derived from atmospheric laboratory laminar and turbulent flames as well as diesel engines. This suggests that the PFA model is mostly independent of combustor and fuel characteristics. The variety of measurements in various flames and engines referenced above provides the basis for this conclusion.

1.2 Scattering Theory for Soot Agglomerates

Two theories to compute the scattering from particles larger than the primary particle diameter have been used in the subject matter disclosed. The first is based on the Rayleigh-Debye-Gans (RDG) theory, which is described in detail by Sorensen, supra, which includes an extensive literature review on this subject. The second theory is one developed by Hull, et al. (Hull, P. Shepherd, I, and Hunt, A., "Modeling Light Scattering from Diesel Soot Particles," Appl. Opt., 43(17): 3433-3441 (2004), incorporated herein by reference in its entirety) using a coupled-dipole scattering model, which shows that the refractive index of a soot agglomerate is simply linearly proportional to the agglomerate density for spherical fill ratios less than 15%, which corresponds to $d_g$ less than 300 nm. Maxwell-Garnet theory, summarized by Sorensen, supra, also shows the same result for one material uniformly diluted within another, in this case carbon primary particles embedded in an equivalent porous sphere. Although aggregates are not generally uniform, this approximation appears to be valid for the range described above.

Using the density relationships of PFA above, one can then relate the density and refractive index to the agglomerate diameter. This then allows one to use full Mie theory to compute the scattering response for agglomerate particles as a function of soot agglomerate diameter and variable refractive index, $\underline{m}(d_g)$, which is also a function of the agglomerate diameter, i.e. $F(d_g, \underline{m}(d_g))$, where F is the non-dimensional scattering cross-section.

This inventor has shown (Holve, D., "Real-Time Optical Smoke Meter (Size and Concentration) for Turbine Engines," Final Report, DOD AEDC PKP, FA9101-04-C-0027, May 18, 2007, incorporated herein by reference in its entirety) that RDG and the coupled-dipole model agree to better than 10% for soot mobility diameters up to 350 nm at 90- and 30-degree scattering angles. Above this diameter, the primary spheres are not uniformly distributed and Mie Scattering assumes a "hard" edge for the equivalent agglomerate sphere, which is not physically true, and thus overestimates agglomerate scattering interference. Thus RDG provides a more accurate estimate of the superposition of scattering from the agglomerate primary particles. Moreover, one may still use the PFA model to describe the mass/density relationship for a model with improved accuracy.

As stated previously, and confirmed in the measurements made by this inventor, gas turbine and small diesel engine soots tend to be smaller than 350 nm, so that either Mie or RDG will work. Ultimately, it will be noted that RDG gives an explicit sensitivity analysis to uncertainties in the primary particle physical and optical properties. The utility of using the Mie theory has been to verify the RDG results.

1.2.1 RDG Scattering Theory 1.2.1.1 Scattering of Monodispersed Particles—The basis of RDG scattering is the superposition of primary particle scattering. The dimensional scattering cross-section for unpolarized light is $\sigma(d_p,\underline{m},\Omega,\theta)$ (cm$^2$) for a primary particle in the Rayleigh range ($d_p \ll \lambda$), and is given by, $$\sigma(d_p,\underline{m},\Omega,\theta)=(2\pi/\lambda)^4(d_p/2)^6 f(m)\Omega(1+\cos^2\theta)/2 \qquad (5)$$

where $d_p$ (cm) is the primary particle diameter, $\Omega$ (sr) is the receiver lens solid angle aperture for scattered light, $\underline{m}$ is the complex refractive index of the primary particle, and $\lambda$ (cm) is the illumination wavelength. In Equation (5), the scattering refractive index function, $f(m)$, is given by:

$$f(m)=|(\underline{m}^2-1)/(\underline{m}^2+2)|^2. \qquad (6)$$

For polarized light, the last term in Equation (5), $(1+\cos^2\theta)/2$, is replaced by 1.0, and scattering becomes uniform in all directions. Experimental measurements performed by this inventor use polarized lasers, and the following equations assume the use of polarized lasers, although unpolarized lasers can also be employed.

The total scattering cross-section of an agglomerate of gyration diameter $d_g$ for a receiver lens aperture $\Omega$ (Sr) is related to the primary particle scattering cross-section at angle $\theta$ by:

$$\sigma(d_g,\underline{m},\Omega,\theta)=n^2\sigma(d_p,\underline{m},\Omega)S(qd_g), \qquad (7)$$

where $\sigma(d_g,\underline{m},\Omega)$ (watts) is the scattering cross-section of a single agglomerate particle, n is the number of primary particles with diameter $d_p$ in the agglomerate, $\sigma(d_p,\underline{m},\Omega)$ (watts) is the scattering cross-section of a single primary particle, $S(qd_g)$ is the structure factor correcting for scattering interactions of primary particles in agglomerate soot particle, q, given by $(4\pi/\lambda)\sin(\theta/2)$, is the scattering wave vector at scattering angle, $\theta$, and $\theta$ is the mean scattering angle for receiver lens.

Equation (7) states that the scattering from an agglomerate is primarily based on the number superposition of primary particles, with a "particle structure" correction ($S(qd_g)$) as the agglomerate increases in size. The standard formulation for PFA, given by Equation (1), is used herein to describe the fractal relationship of n to the agglomerate size, based on the radius of gyration, $d_g$, and the primary particle size, $d_p$.

The total scattered power into a detector depends on the integration of the illumination intensity for all particles in the Gaussian beam sample volume. This integration over the intensity distribution shows that the area average intensity in the sample volume is simply the total laser power, $P_l$, divided by the beam area as defined by the $1/e^2$ beam diameter, $w_o$, or:

$$I_{avg}=4P_l/\pi w_o^2. \qquad (8)$$

This assumes that the beam diameter is constant over the length of the sample volume. The total scattered light at a given angle, $P_{T\theta}$, from a monodisperse population, $N_t$, of agglomerates in the sample volume is then simply:

$$P_{T\theta}=I_{avg}V_s N_t \sigma(d_g,\underline{m},\Omega) \qquad (9)$$

where $V_s$ (cm$^3$) is the particle scattering sample volume, given by $\pi W_o^2 l/4$, $W_o$ (cm) is the $1/e^2$ beam waist diameter of the illuminating laser beam, l (cm) is the length of the sample volume defined by the detector slit width, and $N_t$ (#/cm$^3$) is the average total number of agglomerate particles per unit volume.

The next step is to develop a second relationship that specifies the total mass concentration of a monodispersion of agglomerates of size n (related to $d_g$ and $d_p$), as follows:

$$C_m=N_t m, \qquad (10)$$

where m is equal to n $m_p$ and $m_p$ is given by $(\pi/6)\rho_p d_p^3$.

Ratioing Equations (9) and (10), one obtains:

$$\frac{C_m}{P_{T\theta}} = \frac{N_t n m_p}{I_{avg} V_s N_t \sigma(d_g,\underline{m},\Omega)}. \qquad (11)$$

Equation (11) can be reduced further using the equations above to give an explicit relationship for the mass concentration in terms of conventional soot properties, instrument properties, and a function (referred to herein throughout as the $C_m\#$) which will be shown to be dependent only on the agglomerate gyration diameter if expressed in the following form:

$$\frac{C_m}{P_{T\theta}} = \frac{m_p}{P_l l \sigma(d_p,\underline{m},\Omega) n S(qd_g)} \qquad (12)$$

$$= \left(\frac{\rho_p}{d_p^{3-Df} k_0 f(\underline{m})}\right)\left(\frac{\lambda^{4-Df}}{P_l l \Omega}\right) C_m\#$$

In Equation (12), the terms have been arranged as follows. The first bracketed term $S_p \equiv \{\rho_p/(k_o d_p^{3-Df} f(m))\}$ is a function only of the soot properties, which this inventor has found to be nearly invariant, as discussed further below. The second bracketed term $[\lambda^{4-Df}/(P_l l \Omega)]$ is a function only of the instrument configuration. The $C_m\#$ in this formulation is defined as:

$$C_m\# \equiv \frac{\left(\frac{2k_o}{3\pi^3}\right)\left(\frac{\lambda}{d_p}\right)^{Df}}{n_o S(qd_{go})}. \qquad (13)$$

Although the $C_m\#$ appears to depend on $d_p$, $k_o$, $\theta$, and $D_f$, these parameters are implicit in $nS(qd_{go})$, and it will be shown below that the $C_m\#$ is a dimensionless (and nearly) invariant function only of the scattering ratio $R_{\theta 1/\theta 2}$ at two defined detector angles. This particular formulation uses Equations (1) and (15) to compute $n_o$ and $S(qd_{go})$, consistent with all current methods described in the literature for calculations of soot scattering. However, this approach requires explicit measurement of the constant $k_o$, and as described further below, there is currently an uncertainty of approximately two in this value as measured by various researchers.

A second expression is derived from Equations (7) and (9) for the ratio of scattering at two suitable angles, i.e.:

$$R_{\theta 1/\theta 2}=P_{T\theta 1}/P_{T\theta 2}=S(q_{\theta 1}d_g)/S(q_{\theta 2}d_g). \tag{14}$$

From Equation (14), one can determine a unique expression for $d_g$ in terms of the measured scattering ratio, $R_{\theta 1/\theta 2}$. This means that the $C_m\#$ is also a unique function only of $R_{\theta 1/\theta 2}$.

Once one has the relationship between n and $d_g/d_p$, coupled with the structure function dependence on $d_g$, one can readily compute these moment relationships using various assumptions for the distributions, along with knowledge of values for the fractal dimension, $D_f$ and constant $k_o$. Herein, the empirical structure function recommended by Lin, et al. (Lin, M. Y., Klein, R., Lindsay, H. M., Weitz, D. A., Ball, R. C., and Meakin, P., "The Structure of Fractal Colloidal Aggregates of Finite Extent," J. Colloid Interface Sci., 137: 263-280 (1990), incorporated herein by reference in its entirety) is used expressed in terms of the radius of gyration as:

$$S(qd_g)=\{1+(8/(3D_f))(qR_g)^2+2.5(qR_g)^4-1.52(qR_g)^6+1.02(qR_g)^8\}^{-D_f/8}. \tag{15}$$

This function has been compared with more precise forms based on the density autocorrelation of a fractal aggregate, which does not have a hard sphere boundary. The choice of the density autocorrelation function roll-off (Gaussian) is itself based on best fit with experimental data, but Equation (15) is within 10% of the values used by a variety of researchers (see, for example, Sorensen, supra).

Nicolai, et al., supra, provides an explicit formulation that results on an exact solution for the product nS(q). However, as further explained below, the subject matter disclosed herein provides a more general relationship for $k_o$ and S(q) that is consistent with the empirical expression given in Equation (15). In this analysis, the number of monomers in a monodisperse aggregate is:

$$n=a(d_g/2)^{D_f}. \tag{16}$$

From the typical formulation used by this inventor (see, Holve, supra) and others (see, Sorensen, supra):

$$n=k_o(d_g/d_p)^{D_f}. \tag{17}$$

Therefore, $$k_o=a(d_p/2)^{D_f}. \tag{18}$$

As noted by Nicolai et al., supra, in the limit of large $d_g \gg d_p$, there is an exact solution for a, which is based on the definition of the radius of gyration and particle mass. These quantities in turn are based on the average pair-correlation function of monomers within an aggregate particle, given by:

$$g(r)=[D_f/(4\pi(d_p/2)^{D_f})][(d_p/2)^{D_f-3}]f(r/\xi). \tag{19}$$

where $f(r/\xi)$ is a cutoff function to account for the finite size of the fractal agglomerate. This function is not known exactly, but is assumed to take the form of a "stretched" exponential which has the characteristic that it is close to unity for $r/\xi<1$, and decreases faster than any power law for $r/\xi>1$, i.e.:

$$f(r/\xi)=\exp[-(d_p/2\xi)^\gamma]. \tag{20}$$

Using these relationships in the limit of large $d_g$, Nicolai et al. supra, derives the solution for a as $$a=\{2\Gamma(D_f/\gamma)/\Gamma([D_f+2]/\gamma)\}^{D_f/2}*(D_f/\gamma)\Gamma(D_f/\gamma)[1/(d_p/2)^{D_f}]. \tag{21}$$

Thus combining Equations (16) and (17), results in $$k_o=\{2\Gamma(D_f/\gamma)/\Gamma([D_f+2]/\gamma)\}^{D_f/2}*(D_f/\gamma)\Gamma(D_f/\gamma). \tag{22}$$

This result shows that $k_o$ is not an independent parameter, but rather is dependent on the fractal dimension, $D_f$ and the sharpness of the cutoff function, $\gamma$.

From the second mass balance equation, Nicolai et al., supra, determines the relationship for $\xi$ from:

$$R_g^2=\xi^2\Gamma([D_f+2]/\gamma)/2\Gamma(D_f/\gamma). \tag{23}$$

Figure 6:
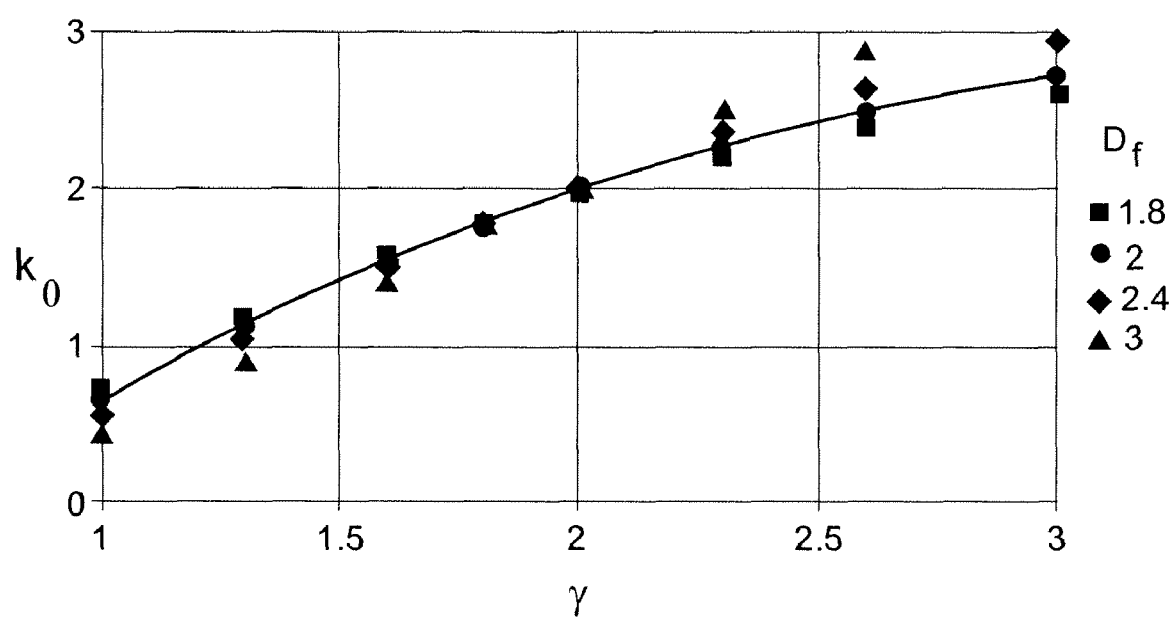
FIG. 6 illustrates the variation of $k_o$ as a function of $\gamma$, with $D_f$ as a parameter.

If one calculates $k_o$ as a function of $\gamma$, with $D_f$ as a parameter, one obtains the results shown in FIG. 6. As shown in FIG. 6, $k_o$ has a weak dependence on $D_f$ which are all identical for a Gaussian distribution with $\gamma$ equal to 2. Although it appears that another unknown ($\gamma$) has been merely substituted for $k_o$, it will be shown herein below that the product nS(q) is virtually independent of the choice of feasible values of $\gamma$.

From Equation (12) it is the product nS(q) that is important for computing the mass concentration. Using the general relationship for g(r), this product for general conditions is given by:

$$nS(q)=1+D_f/(d_p/2)^{D_f}*\int_{d_p/2}^{\infty} r^{D_f-1}\exp(-[r/\xi]^\gamma)\sin(qr)/qr\,dr. \tag{24}$$

Making the change of variable $x=2r/d_p$, Equation (24) becomes:

$$nS(q)=1+D_f\int_1^\infty x^{D_f-1}\exp(-[xd_p/2\xi]^\gamma)[2\sin(qd_p x/2)/qd_p x]dx. \tag{25}$$

Note that in Equation (25), there is no explicit definition of $k_o$. The only parameters are q, $d_p$, and $\gamma$. In the limit of $d_g \gg d_p$, $$nS(q)=D_f\Gamma([D_f-1])\sin[(\pi/2)(D_f-1)][(qd_p/2)^{-D_f}]. \tag{26}$$

As defined herein, the dimensionless parameter $C_m\#(q)$ is independent of $d_p$ and is a function only of the agglomerate diameter, $d_g$, the fractal dimension, $D_f$, and instrument parameters $\lambda$ and $\theta$, which are fixed for a given instrument geometry. That is:

$$C_m\#(q)=(2/3\pi^3)(\lambda/d_p)^{D_f}/\{nS(q)\}. \tag{27}$$

Note the similarity of Equations (13) and (27), the only difference being the explicit inclusion of $k_o$ in Equation (13), which used the empirical relation for S(q), given by Equation (15). However, Equation (12) shows that $k_o$ embedded in the soot parameter term divides out the $k_o$ in Equation (13). The explicit inclusion of $k_o$ in the formulation of Equation (12) was based on the conventional method of calculation for n in the research literature, but which requires choice of uncertain experimental values of $k_o$ given in the literature.

Figure 7:
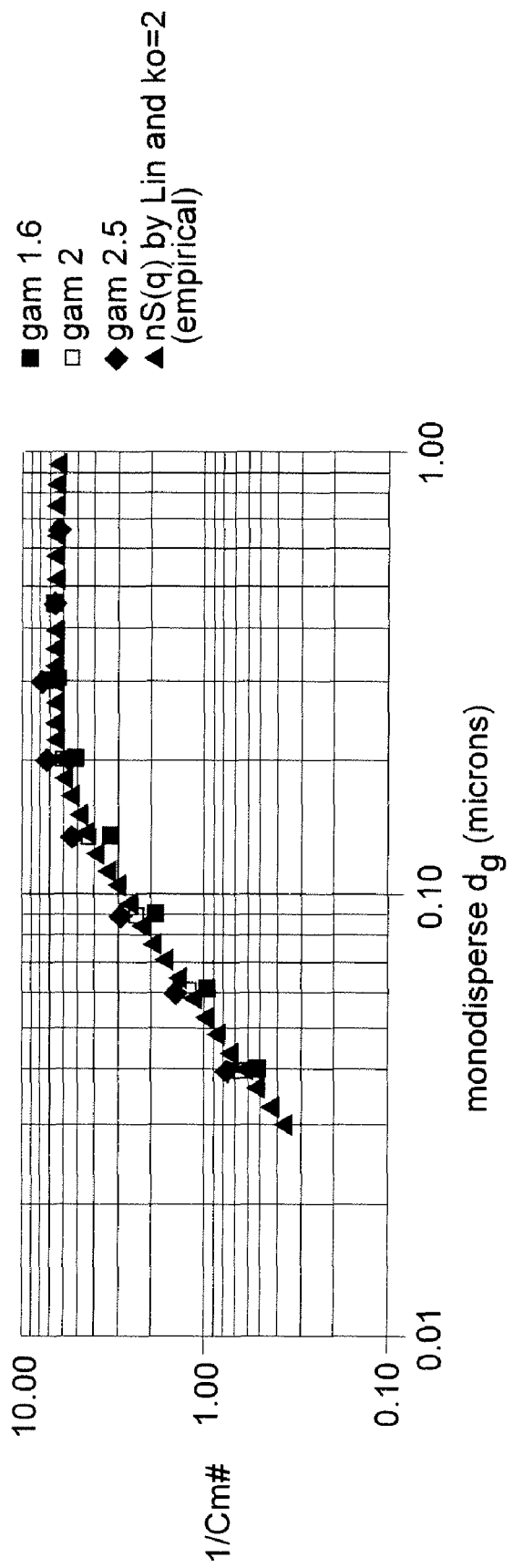
FIG. 7 illustrates the variation of inverse $C_m\#$ as a function of $d_g$ for a range of cutoff function parameters $\gamma$ for q=14 and $D_f=1.8$.

Using Equation (23) to define $\xi$ in terms of $2R_g=d_g$, one can numerically integrate Equation (25) to obtain a unique function dependent only on $d_g$ for specified values of $\lambda\theta$, and $D_f$. The inverse $C_m\#$ is graphed in FIG. 7. The important result here is that the $C_m\#$ is virtually independent of the choice of the cutoff function parameter, $\gamma$, for values in the range of the Gaussian cutoff function, $\gamma=2$, used for most current analyses. In contrast to FIG. 6, where $k_o$ varies significantly with the choice of $\gamma$, the product nS(q) is nearly invariant, and $k_o$ does not appear explicitly, but rather is embedded as a function of $D_f$ and $\gamma$. Also shown in FIG. 7 is a comparison of the commonly used empirical curve fit function for S(q) of Liu et al., supra, based on $\gamma=2$, and the calculated value of $k_o=2$ from FIG. 6. The two results are in excellent agreement. These results show a $C_m\#$ variation of less than 15% for $\gamma$ ranging from 1.6-2.5, which encompasses the range of literature values used by various researchers. Extreme values of γ increase the variation, but no more than ±30%.

Thus this inventor concludes that the quantity nS(q) is only weakly dependent on assumptions of the detailed cutoff function, whereas n and S(q) themselves show much greater variation. For mass concentration measurements, the subject matter disclosed herein shows that the product nS(q) is a more fundamental and invariant expression, uniquely developed by Holve, supra. While Nicolai, et al., supra, have developed a theoretical expression for the mono-disperse nS(q), they have developed different moment functions for the practical polydisperse case only for n and $R_g$ independently. In the following, this inventor further develops the appropriate moment functions for nS(q) and $C_m\#$, for polydisperse size distributions.

Equation (12) can now be expressed as:

$$\frac{C_m}{P_{T\theta}} = \left(\frac{\rho_p}{d_p^{3-D_f} f(\underline{m})}\right)\left(\frac{\lambda^{4-D_f}}{P_l/\Omega}\right) C_m\#(q). \quad (28)$$

where the $C_m\#$ is now defined in Equation (27). Equations (12) and (28) are consistent with each other, given their respective $C_m\#$ definitions.

For defined instrument values of (λ,θ), the $C_m\#(q)$ is a unique and invariant function of $d_g$ if $D_f$ is known (as the literature shows for soot). In addition, the results from Nicolai, et al., supra, confirm that the $C_m\#$ is not very sensitive to the assumed choice of γ for the cutoff function. It is noted that measurement of $k_0$ effectively defines γ, or, alternatively, if a value of γ is chosen to define S(q), (e.g., the Gaussian cutoff, γ=2), then a unique value of $k_o$ is defined. For γ=2, $k_0$ must be 2.0 (FIG. 6) to satisfy the mass balance relationships resulting in Equations (22) and (23).

This example is based on use of a monodispersion, yet similar results can be derived for the polydisperse case, where the mass mean diameter is used to define $d_{go}$ and $n_o$, and a moment function ratio is based on the typical agglomerate distribution width. This moment function ratio is relatively invariant for the well-known distribution functions that occur in practice, and results in a polydisperse $C_m\#$, which is nearly invariant for typical agglomerate size distributions occurring in practical applications.

The primary uncertainties remaining in calculating the particle mass concentration, $C_m$, are the soot properties, $f(m)/\rho_p$, and the primary particle size, $d_p$. This inventor has proposed that the refractive index effect has less variance when accounting for the variations in particle density, which have not been measured by researchers, and thus can be defined by reference for pure carbon. In regards to $d_p$, it is noted that a variety of measurements on engines and research flames shows limited variation in the primary particle size for near stoichiometric conditions, which are used for most industrial engines.

1.2.1.2 Scattering of Polydisperse Soot—For polydispersed soot a similar derivation as described above is followed, except, for the general polydisperse case, one sums the contributions from each particle size class of the distribution for the total mass and total scattering. Thus, the total scattering cross-section, $\sigma_p$, of the polydisperse distribution is given (from Equation (7)) by:

$$\sigma_p = \Sigma \Delta N_i \sigma(d_{gi},\underline{m},\Omega,\theta) = \Sigma \Delta N_i n_i^2 \sigma(d_p,\underline{m},\Omega) S(qd_{gi}), \quad (29)$$

where $\Delta N_i$ is the number of particles in the subclass i, and the sum, Σ, is taken over the entire particle size range. As described in Appendix A, and in the following, there are a number of different distribution functions that can be used to characterize typical soot distributions. Nevertheless, it is shown herein that the ultimate result for computing the $C_m\#$ and mean diameter $d_{go}$ is insensitive (<±10%) for measured soot size distributions.

Similarly, from Equation (10), the total mass concentration of the distribution is given by:

$$C_m = \Sigma \Delta N_i n_i m_p. \quad (30)$$

Each of these equations can be normalized by the mean values of the distribution parameters, $d_{go}$, $n_{go}$, and the total number of particles in the distribution, $N_t$, thus:

$$\sigma_p = N_t n_{go}^2 S(qd_{go}) \Sigma \Delta N_i n_i^2 \sigma(d_p, \underline{m},\Omega) S(qd_{gi})/N_t n_{go}^2 S(qd_{go}). \quad (31)$$

Similarly, $$C_m = N_t n_{go} \Sigma \Delta N_i n_i m_p / N_t n_{go}. \quad (32)$$

The summation terms are thus defined as moment functions and the solution for total scattering and mass follows the same analysis (Equations (5)-(14)) as previously described to give the same results as shown in Equations (13) and (14), except that the solution is now expressed in terms of the moment functions and the mean values of the parameters $n_{go}$ and $d_{go}$. That is:

$$C_m\# \equiv \left(\frac{M_1}{M_{2\theta 1}}\right) \frac{\left(\frac{2}{3\pi^3}\right)\left(\frac{\lambda}{d_p}\right)^{D_f}}{n_o S(qd_{go})}, \quad (33)$$

where the non-dimensional first and second moment functions are:

$$M_1 = \sum \left(\frac{\Delta N_i}{N_t}\right)\left(\frac{n_i}{n_{go}}\right) \quad (34)$$

and $$M_{2\theta} = \sum \left(\frac{\Delta N_i}{N_t}\right)\left(\frac{n_i}{n_{go}}\right)^2 \left(\frac{S(q_\theta d_{gi})}{S(q_\theta d_{go})}\right). \quad (35)$$

In Equation (33), one defines the $C_m\#$ for a specific light collection angle, $\theta_1$, which, in the exemplary embodiment described herein, is chosen to be 90 degrees, but either detector angle can be used.

The subscript "o" refers to the mean value of gyration diameter or number of primary particles determined by the scattering ratio measurement, which for an agglomerate polydispersion becomes:

$$R_{\theta 1/\theta 2} = \left(\frac{M_{2\theta 1}}{M_{2\theta 2}}\right)\left(\frac{S(q_{\theta 1} d_{go})}{S(q_{\theta 2} d_{go})}\right). \quad (36)$$

This equation gives an implicit direct relationship between $d_{go}$ and the measured scattering ratio $R_{\theta 1/\theta 2}$ at the two scatter angles, that is:

$$\frac{C_m}{P_{T\theta}} = \left(\frac{\rho_p}{d_p^{3-Df} f(\underline{m})}\right)\left(\frac{\lambda^{4-Df}}{P_l l \Omega}\right) C_m\#(qd_{go}). \qquad (37)$$

Note that in comparison to Equation (12), $k_o$ is no longer an explicit parameter, but is divided out by the $k_o$ in the soot parameter term of Equation (12).

The formulation described in Equations (36) and (37) provides a new and unique solution to the measurement and interpretation of mass soot concentrations. As those of ordinary skill in the applicable arts will appreciate it, these expressions show a simple, but yet fundamental relationship for the mass concentration in terms of $d_{go}$, which is a function only of the measured scattering signals at two detectors and has not been discovered until the present work.

To solve this problem generally, one only needs to model the polydisperse distribution shape for the aggregates. In the analysis disclosed herein, a mathematically well-characterized agglomerate size distribution function is favored to determine the total scattering. Experimental measurements, as shown by Koylu et al. and Sorensen and Feke, supra, confirm that a lognormal size distribution function (Appendix A) is appropriate for number, area, and volume distribution characterization. At the same time, scaling distributions based on n are also used, are similar and can be related to the Rosin-Rammler or Weibull distributions. The lognormal and Rosin-Rammler distributions are defined and compared in Appendices A and B, while scaling distributions are described in the text below. All can be shown to be sufficiently similar that the specific choice of a typical distribution has less than 10% effect on the determination of the mass concentration.

As outlined above, soot agglomerates have unique properties, which are based on random collections of uniform primary particle elements of specified diameter, $d_p$, which collide to form agglomerate structures with $n_i$ elementary particles, similar to that shown in FIG. 4. In contrast aerosol particles are made up of condensed solid droplets or attrition particles, which are continuous solid particles without internal gaps or open spaces. As such their scattering properties are defined by Mie theory, and these particles are treated as one single uniform scattering element. Therefore, the equations leading to the specific development of the $C_m\#$ hereinabove apply only for agglomerate materials. However, those of ordinary skill in the applicable arts, after reviewing the subject matter disclosed herein throughout, will appreciate that similar expression may be obtained for the application of the disclosed apparatuses and methods for the measurement of aerosol particles.

Scaling function distributions have been used previously by various researchers (see, for example, Sorensen, supra) to describe the distributions of soot agglomerates, which evolve in a self-preserving fashion with time. For sufficiently long aggregation periods, the aggregate size distribution has the following form, independent of time:

$$p(x_i) = A x_i^{-\tau} \exp(-\alpha x_i), \qquad (39)$$

where $x_i$ is equal to $n_i/n_o$, $n_i$ is the number of monomers in a cluster aggregate i, $n_o$ is the mean cluster size of the distribution, $\tau$ is the scaling parameter, $\alpha = 1 - \tau$, and A is equal to $\alpha^{2-\tau}/\Gamma(2-\tau)$.

Note that the scaling distribution is similar to the Rosin-Rammler distribution expressed in terms of the diameter, with the exponent p (see, Appendix A) being equal to the fractal dimension, $D_f$. In the nomenclature for the agglomerate size distribution used herein, $$\Delta N_i/N_t = p(n_i/n_o)\Delta n_i/n_o. \qquad (35)$$

Figure 8:
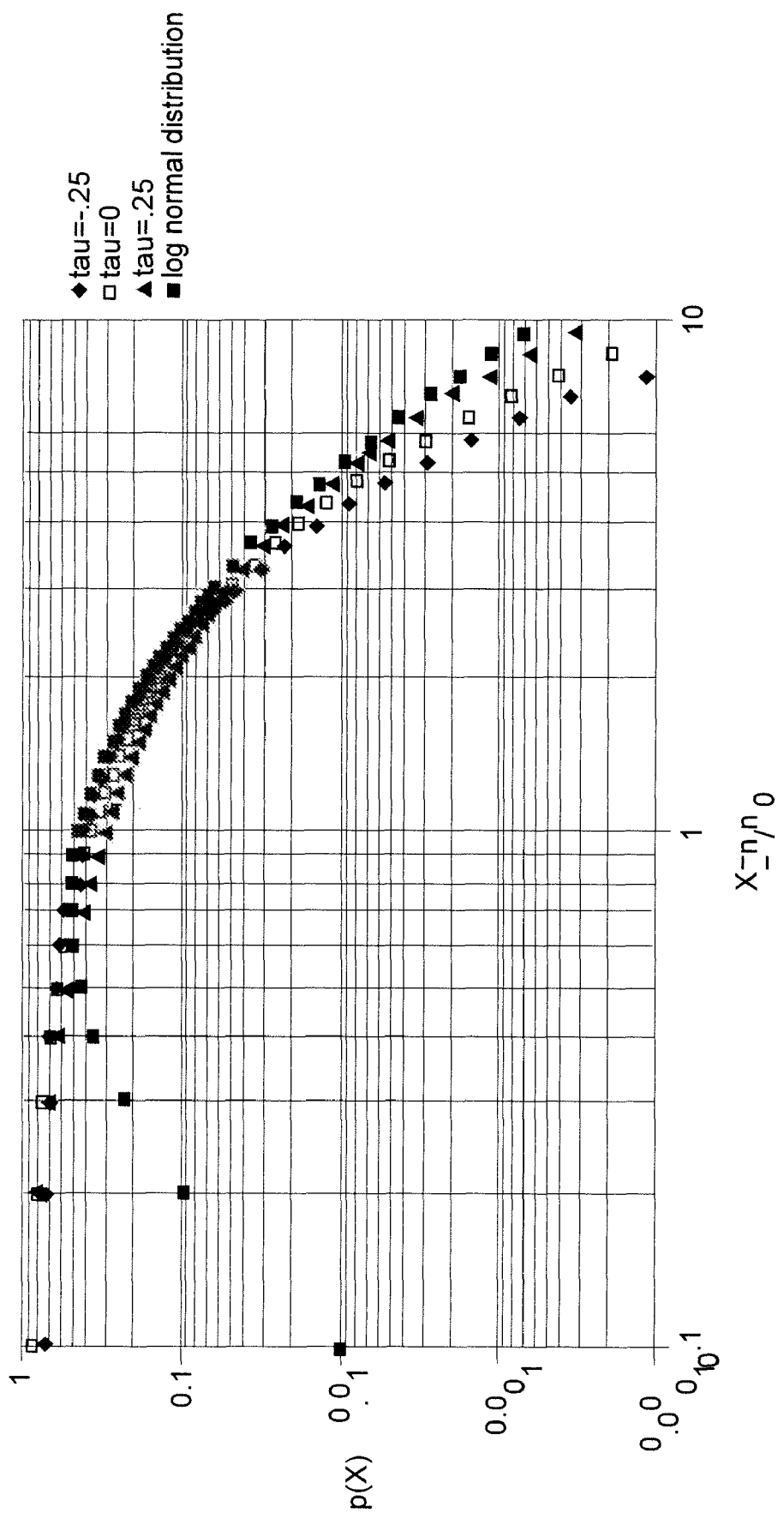
FIG. 8 illustrates distributions of scaling functions for cluster agglomerates for several values of the scaling parameter, $\tau$, together with a log-normal distribution for sigma=1.75.

FIG. 8 shows $p(n_i/n_o)$ graphed as a function of the parameter $\tau$, which has been measured for soot distributions, as noted by Sorensen, supra. FIG. 8 also includes a distribution for the lognormal function with $\sigma = 1.75$. Note that the lognormal function is approximately similar to the scaling function for $x > 0.5$, although it rolls off at smaller values of $x_i = n_i/n_o$. Because $M_1/M_2$ are first to second order (in n) moment functions and are ratioed, this difference has little effect on the final computed values in Equations (34)-(37), which will be demonstrated below.

In the limit of small and large values of $n_o$, $M_1/M_2$ reduce to unity and the $C_m\#$ reduces to the simple mono-disperse results. The limiting cases for small and large values of $n_o$ will now be considered.

Small $n_o$ and $M_1/M_2 = 1.0$ for agglomerates collapsing to mono-disperse primary particle distribution—In practice, this assumption is not accurate, but it is known that the primary particle size distribution is relatively narrow, with a standard deviation of approximately 20%, with a log-normal standard deviation of $\sigma \sim 1.2$ (see, for example, Hu and Koyly, supra, and Dankers, S. and Leipertz, A., "Determination of primary particle size distributions from time-resolved laser-induced incandescence measurements," Applied Optics, 43(18): 3726-3731 (2004), which is incorporated herein by reference in its entirety). This is less than mobility size measurements of agglomerates with values of $\sigma \sim 1.6$-2.0 (see, for example, Whitefield, P., Hagen, D., and Lobo, P., "PM Characterization of Aircraft Engines," Project APEX, presented at 24th AAAR Conference, Austin, Tex., Oct. 20, 2005, which is incorporated herein by reference in its entirety). Many researchers have noted that primary particles have a narrow relative and absolute size distribution for a variety of combustion systems. Specifically, Kazakov and Frenklach (see, for example, Kazakov, A and Frenklach, M., "Dynamic modeling of Soot Particle Coagulation and Aggregation: Implementation with the Method of Moments and Application to High-Pressure lamina Premixed Flames," Combustion and Flame 114:484-501 (1998), which is incorporated herein by reference in its entirety) have modeled the condensation/aggregation of soot particles. Their results show that the primary particle sizes quickly reach a constant size, where the primary particles "freeze out" in size at values of 25-35 nm. Subsequent soot growth is by agglomeration of these primary particles, and in practice the smallest soot agglomerates are typically larger than 100 nm. This observation is relevant for STAR measurements, since Equation (20) shows an approximately inverse linear dependence on primary particle size. Based on literature values, this inventor has chosen a fixed value of $d_p = 35$ nm, which is mass-weighted towards the upper end of number mean measurements occurring in the latter stages of flames and engines. This assumption seems to be accurate to within ±15%, based on the range of experimental and theoretical measurements for various combustion systems described above, and for different colloidal materials, including titania and silica (see, for example, Wang, G. and Sorensen, C., "Experimental test of the Rayleigh-Debye-Gans theory for light scattering by fractal aggregates," Applied Optics, 41(22): 4645-4651 (2002), which is incorporated herein by reference in its entirety).

Large $n_o$ and $M_1/M_2 = 1.0$ for any agglomerate distribution—For large values of $n_o$, the product of $n_o S(qd_{go})$ becomes a constant.

Next the general polydisperse and monodisperse values of the $C_m\#$ are computed, using typical values for the range of primary particle size, fractal dimensions, and polydisperse distribution values.

Figure 9:
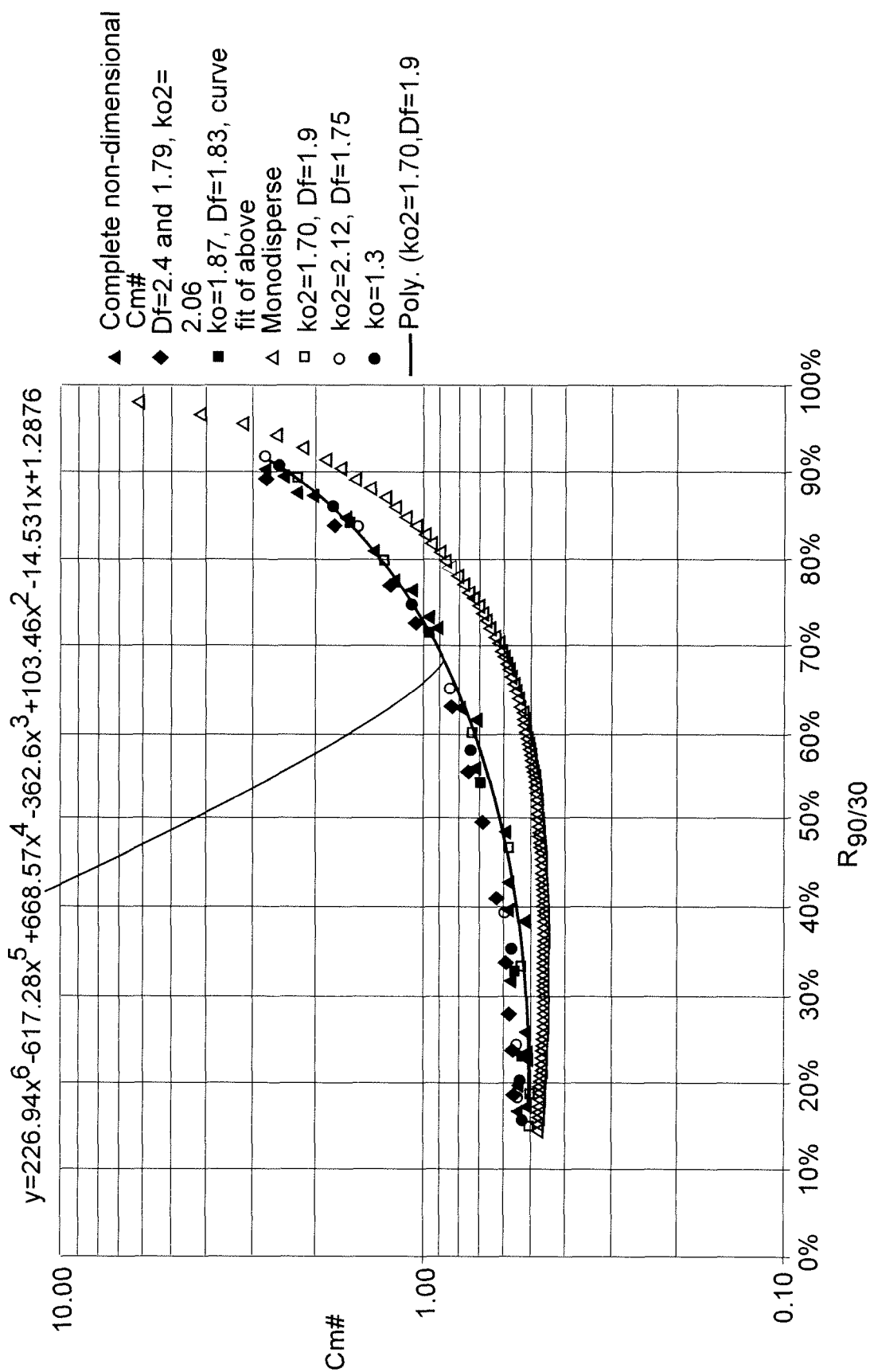
FIG. 9 illustrates calculation results of the $C_m\#$ for both polydisperse and monodisperse soot using typical values for the fractal dimension measured in the literature between 1.7 and 1.9.

These results are shown in FIG. 9, which contain calculations of $C_m\#$ for both polydispersed and monodispersed soot (solid line), using typical values for the fractal dimension measured in the literature between 1.7 and 1.9. As shown in FIG. 9, computations confirm that the $C_m\#$ of Equation (37) is nearly invariant with primary particle size, and scaling parameter, $\tau$, for a given light collection angle, $\theta$. The sixth-order polynomial fit included in FIG. 9 is an exemplary embodiment of the nearly invariant function that represents the dependency of $C_m\#$ on the ratio of scattered light, as previously described. It should be understood by those of ordinary skill that in the polynomial fit shown, x stands for the scatted ratio plotted as the abscissa and y is the $C_m\#$ plotted as the ordinate. In addition, as already stated, the sixth-order polynomial fit represented in FIG. 9 is included here only as a exemplary embodiment of the disclosed nearly invariant function, other forms of curve fit, including, but not being limited to, lower or higher order polynomials or a numerical curve fit may be used to represent the nearly invariant advantageous feature of the variation of $C_m\#$ as a function of the ratio of scattered light.

The important result is that, for the feasible ranges of fractal dimensions known in the literature (1.7-1.9), there is minimal effect on the $C_m\#$. This inventor also confirms that there is minimal effect of the choice of primary particle size, and laser wavelength. Finally it is shown herein that variations in the assumed distribution width also have minimal impact, consistent with the analysis in Appendix B. In sum, all these parameter variations give less than ±10% variation in the $C_m\#$ for the range of $D_f$ described above. This result shows the value of this defined "invariant" function which is dependent only on the measured two angle scattering ratio, $R_{\theta1/\theta2}$. In the disclosed formulation, the $C_m\#$ is general, for all values of primary particle size, distribution width, $\tau$, and for the range of $D_f$ for soot.

It is noted that for $R_{90/30}<40\%$ ($d_{go}>150$ microns), the $C_m\#$ is essentially constant, and the computation of the mass concentration, $C_m$, is dependent only on the scattering signal from the large-angle detector (i.e., the exemplary angular position of 90 degrees shown herein). This has a potentially important practical implication for certain applications where it is known that $d_{go}>150$ microns. One can then implement a very simple instrument with a single large-angle detector (e.g. 90 degrees) to measure the mass concentration, $C_m$, although one cannot determine $d_{go}$. Extending this analysis further, it can be shown that for large values of the product $qd_g$, one can achieve the limit of constant $C_m\#$ for smaller values of $d_{go}$ less than 100 nm. Using a shorter wavelength laser, combined with a larger scattering angle detector, e.g. 145 degrees, the critical agglomerate diameter for constant $C_m\#$ can be reduced proportional to $\sin(\theta/2)$, and the inverse laser wavelength, $\lambda$. The measurements performed by this inventor and others have shown that most engine soots have a mean agglomerate size greater than 100 microns. Thus using a laser wavelength in the ultraviolet to blue range at, for example, $\theta=145$ degrees would allow one to implement a single backscatter detector instrument for accurate mass concentration measurement without the need for agglomerate diameter measurement.

Based on the approached disclosed herein those of ordinary skill will note that monodisperse results are not substantially different from the polydisperse results and agree with the polydisperse values in both the small and large limits. Because scattering is weighted towards larger particles, it is clear that a polydispersion will have higher values of the $C_m\#$ than for the monodispersion. The $C_m\#$ is independent of the soot and instrument properties, being dependent only on the measured two detectors signal ratio (e.g. $R_{90/30}$). The importance of this invariance is discussed further below. Given that most engine soots have a limited range of agglomerate sizes, the $C_m\#$ has been computed herein over the size range of n=6-400, using Equation (24) for typically measured values of $D_f$ and feasible values of the cutoff function $\gamma$.

Figure 10:
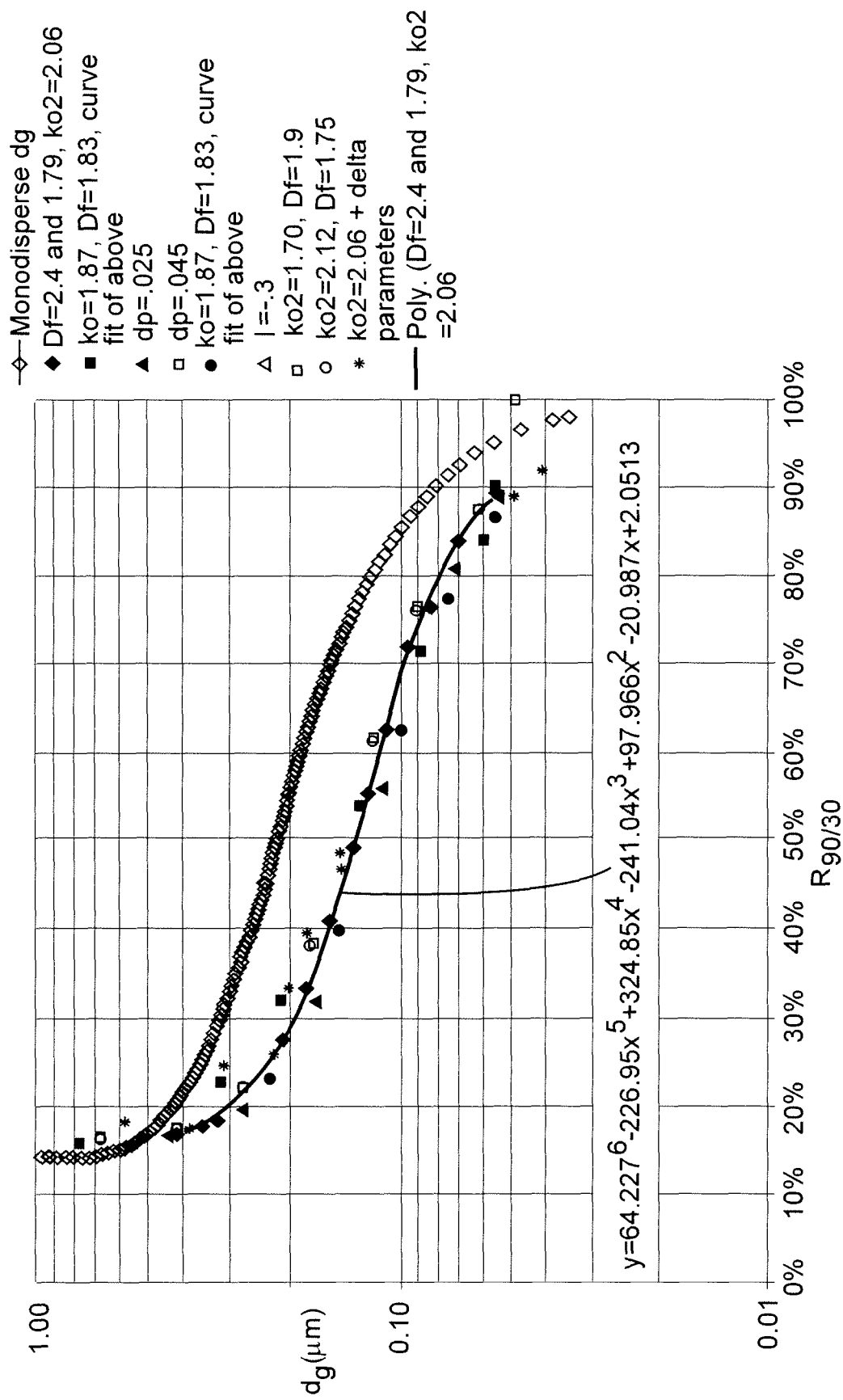
FIG. 10 illustrates the variation of the gyration diameter as a function of the two-angle scattering ratio, $R_{90/30}$, for polydisperse and mono-disperse assumptions for the particle aggregate size distribution for different soot properties.

FIG. 10 shows the corresponding gyration diameters computed as a function of the $R_{90/30}$ ratio used in the measurements performed by this inventor. The sixth-order polynomial fit included in FIG. 10 represents an exemplary embodiment of another nearly invariant function that represents the dependency of the gyration diameter on the ratio of scattered light. It should be understood by those of ordinary skill that in the polynomial fit shown, x stands for the scatted ration plotted as the abscissa and y is the gyration diameter plotted as the ordinate. In addition, as already stated, the sixth-order polynomial fit represented in FIG. 10 is included here only as a exemplary embodiment of the disclosed nearly invariant function representing the variation of the gyration diameter as a function of the ratio of scattered light and other forms of curve fits, including, but not being limited to, lower or higher order polynomials or a numerical curve fit, may be used to represent the nearly invariant advantageous feature of the variation of the gyration diameter as a function of the ratio of scattered light. Again, there are minimal effects of parameter assumptions on this invariant function for optical gyration diameter. As above, the monodisperse relationship is not significantly different, and similar to the discussion above, a polydisperse mean size scatters more light than the equivalent monodisperse size, except in the large and small limits.

1.2.3 Soot and Instrument Properties

The primary particle properties are characterized by the first bracketed term of Equation (37), $S_p=\{\rho_p/d_p^{3-D_f}f(m)\}$. Both the refractive index and even the primary particle size are dependent on the particle density. The density is well known for pure carbon, with a value of 2 gm/cm$^3$. Measurements by Park, et al. and Slowik, et al., supra, give values of 1.7-1.8 g/cm$^3$ for soot primary particles. A range of refractive index measurements of carbon soots have been obtained, and are summarized by Sorensen, supra, in Table 1 below. One can see that there is a less than 50% variation in the scattering values of f($\underline{m}$). One problem in characterizing the appropriate value of refractive index for combustion soot that this inventor has observed is that the refractive index measurement is not correlated with a measured value of the particle density, except for the pure carbon case with $\underline{m}=1.7-0.7i$.

TABLE I

Extinction, E($\underline{m}$), and scattering, f(m), as a function of measured refractive indices, ($m_1$-$im_2$), Sorensen, supra.

| $m_1$ | $m_2$ | E($\underline{m}$) | f(m) |
|---|---|---|---|
| 1.57 | 0.56 | 0.260 | 0.217 |
| 1.75 | 0.5 | 0.200 | 0.242 |
| 1.9 | 0.55 | 0.193 | 0.298 |
| 1.7 | 0.7 | 0.285 | 0.305 |
| 1.7 | 0.8 | 0.320 | 0.352 |
| 1.85 | 0.4 | 0.149 | 0.245 |
| 1.77 | 0.63 | 0.244 | 0.291 |
| 1.53 | 0.38 | 0.184 | 0.147 |
| 1.54 | 0.48 | 0.229 | 0.180 |
| 1.55 | 0.8 | 0.366 | 0.332 |
| 1.69 | 0.58 | 0.242 | 0.253 |

Figure 11:
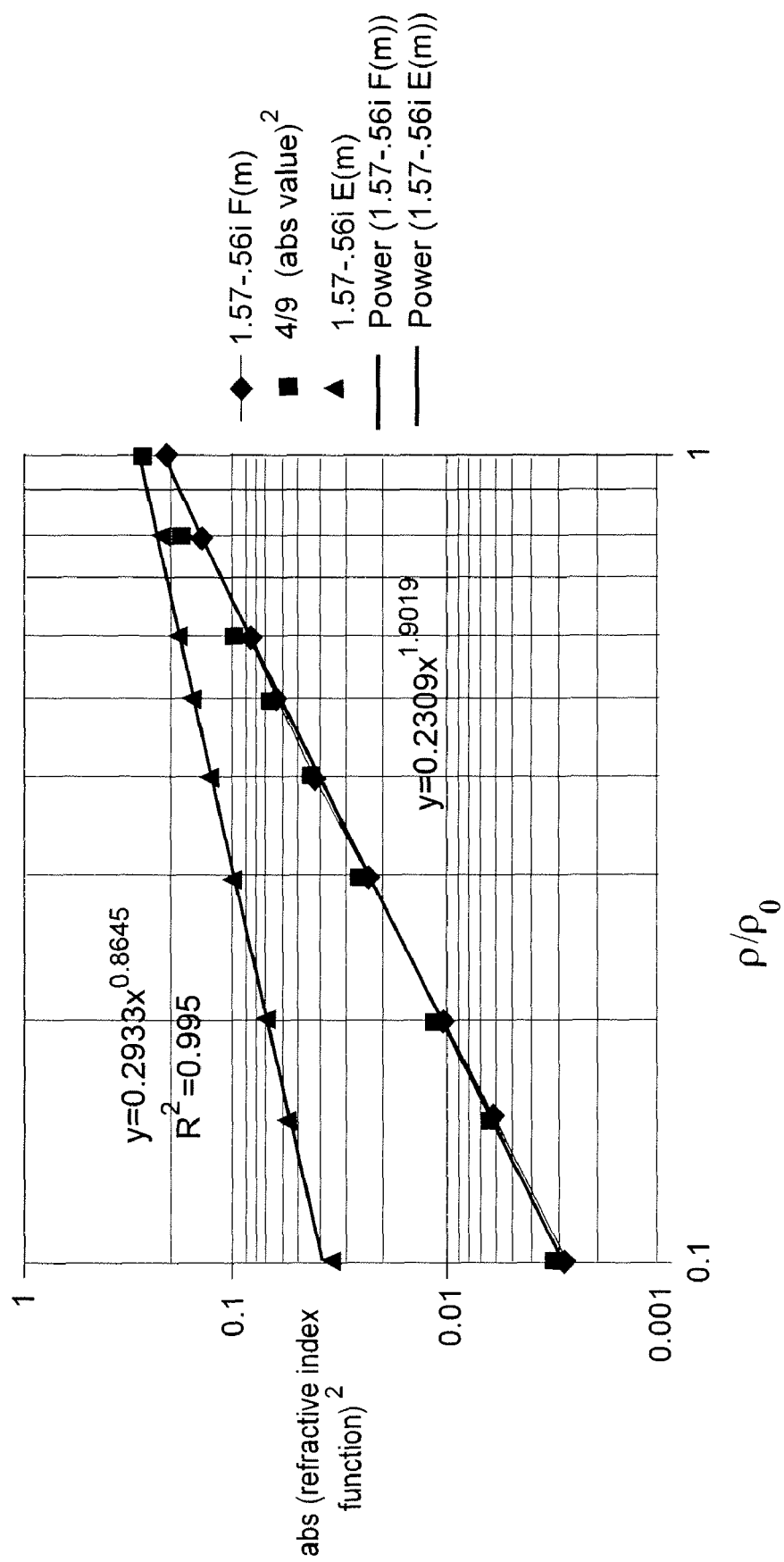
FIG. 11 illustrates the variation of extinction coefficient, E(m), and scattering coefficient, f(m), as a function of aggregate density relative to primary particle density.

Whatever value of refractive index that is used herein as the reference value for the primary particles, a relationship for the refractive index as a function of the agglomerate density may be developed using the result from Hull and Hunt, supra, that the complex refractive index is linearly related to the effective particle density similar to Maxwell-Garnet effective medium theory. Although agglomerates are not strictly uniform, Hull and Hunt, supra, found that this approximation worked well for density filling greater than 15%. Using this result and computing E(m) and f(m) gives the result shown in FIG. 11. The result is the formula, $$f(\underline{m})/f(\underline{m}_r) = (\rho/\rho_r)^{1.9}, \quad (40)$$

where the subscript r corresponds to a fundamental reference carbon refractive index, corresponding to a specific density of 2.0 gm/cm$^3$. Similarly, the extinction parameter is given by:

$$E(\underline{m})/E(\underline{m}_r) = (\rho/\rho_r)^{0.86}. \quad (41)$$

This relationship has been applied to computing the refractive index for agglomerates, using the full Mie theory, and agrees quite well with RDG theory up to $d_m=300$ nm. In a similar fashion, this relationship will also apply to primary particles with densities lower than the theoretical upper limit for elemental carbon.

Returning to the pure carbon case, the ratio $f(\underline{m})/\rho_p$ is equal to 0.153. Given the semi-crystalline nature of condensed soot, the density for combustion soot is generally taken to be less than that of elemental carbon. The median value from Table I is 0.242, and if a more likely value of soot density is used (e.g., $\rho_p=1.7$), one obtains $f(\underline{m})/\rho_p=0.142$, within 10% of the pure carbon value. Calculating the mass concentration $C_m$ is thus less sensitive to uncertainties in the refractive index than calculating the volume fraction (used by De Luliis et al., supra, and others), which does not ratio out the density.

Park et al, Slowik, et al. and Kazakov and Frenklach, supra, have shown that the primary particle is relatively invariant (less than ±20%) for a wide range of combustion conditions. Given that both $d_p$ and $f(m)/\rho_p$ are essentially constant, then $S_p$ will be nearly invariant for a wide range of combustion systems. The measurements disclosed herein below support this proposition.

The second term in brackets for Equation. (37) refers to the scattering measurement and instrument parameters, $[\lambda^{4-Df}/(P_l 1\Omega)]$. The laser wavelength is well-defined, and the other three parameters, laser power, sample volume path-length, and receiver aperture, along with the implicit detector gain embedded in $P_{7\theta}$ are all accurately determined by measuring the Rayleigh scattering from air or propane (see, for example, Sorensen, supra). This inventor has performed extensive calibration tests using Rayleigh scattering and comparing these results with absolute scattering from a single mode fiber source with a known power input on the order of nano-watts, similar to that from actual soot scattering. These two methods agree within 10%, and confirm that the Rayleigh scattering method is the simplest and most reliable method for measuring all instrument parameters. Table II summarizes the standard instrument parameters, and accuracy and precision uncertainty estimates for $C_m$.

The largest contributors to absolute accuracy are the uncertainties in the soot property parameters within $S_p=\{\rho_p/\{d_p^{3-Df}f(\underline{m})\}\}$. At present, the major contribution to uncertainty is the "true" value of $d_p$. Although individual values of $S_p$ may have greater variance, the analysis disclosed herein has shown that the overall product most likely has less variation, based on the close correspondence of results by Slowik et al. and Park, et al, supra. Experimental measurement uncertainties add only 1% to the overall accuracy uncertainty. The primary experimental uncertainty in the $C_m$# propagates through the measurement of $R_{90/30}$ and ranges from 5% for large particles to 9% at $R_{90/30}=0.85$, increasing further at higher ratios. This effectively defines the lower size limit of feasible measurements with STAR, i.e. for soot particles with mean gyration diameters above 60 nm.

TABLE II

STAR parameters, instrument values, and estimated mass concentration uncertainty as a function of input parameters and measurables.

| Parameter | Instrument values | Accuracy % | Precision % |
|---|---|---|---|
| $P_t$ | watts | 5% | 2% |
| $P_l$ | watts | 3% | 2% |
| $R_{90/30}$ | — | 5% | 3% |
| $\rho_p/\{d_p^{3-Df}f(\underline{m})\}$ | gm/cm$^4$ | 20% | 0% |
| $\Theta$ | 90 deg | 5% | 0% |
| $\Omega$ | 0.102 Sr | 5% | 0% |
| $\lambda$ | 635 nm | 0% | 0% |
| L | .80 cm | 4% | 0% |
| $C_m$# | — | 7% | 5% |
| Total $C_m$ uncertainty | | 24% | ±6% |

In addition to primary particle properties, this inventor has estimated the uncertainties of the fractal dimension, $D_f$, and distribution width, $\tau$, for scaling distributions or $\sigma$ for a Gaussian distribution, in defining the $C_m$#. As it has been shown above in the computation of the $C_m$#, variations in the distribution width tend to cancel out in the ratio of the moment functions defined in Equations (34) and (35). Similarly, variations in the power $D_f$ also tend to divide out dimensionally in the $C_m$#, as shown in Appendix B. Overall, variations in $D_f$ of ±7% give less than ±7% variation in the computed $C_m$#. This is one of the advantageous features of the $C_m$# analysis, showing that uncertainties in the distribution width parameter, $\tau$, and $D_f$ tend to cancel out, reducing sensitivity to their precise measurement. For specific types of combustion systems, the variance in $\tau$ and $D_f$ may be even less. Similarly, it is likely that the primary particle size variance for a given combustion device is less than that measured over a wide variety of flames and engines, as assumed above.

The accuracy of the gyration diameter, $d_{go}$, measurement is similar to that of the $C_m$#, with the uncertainty varying from 5% at large particles (less than 400 nm) and increasing to 12% at 60 nm. The underlying accuracy of the theory is primarily based on the structure function, which is estimated to be on the order of 10%. Thus the overall uncertainty of the size measurement is ±10-15%, increasing for smaller particles less than 60 nm.

1.2.4 Theory Summary

In summary, Table II provides a framework to verify the validity of the STAR method. The analysis presented herein agrees with recent measurements (see, for example, Neer and Koylu, Koylu et al., and Hu et al., supra), which give a value of $k_o=2\pm20\%$. Evaluation of the refractive index for combustion soots combined with density would also lead to more accurate measurements, but the apparent uncertainty for scattering measurements is less than previously assumed because all soot properties are embedded as one product in the soot property parameter, $S_p$. Although the primary particle diameter, $d_p$, must be assumed for low concentration applications where measurement by extinction combined with scattering methods are infeasible, there are many results showing that the variance of $d_p$ is small (±20%). The fractal dimension appears to be stable for a wide variety of combustion systems and fuels with a value of 1.8 (±6%). The aggregate particle size distribution widths are also well-known, and at the same time any variations in the particle distribution width tend to cancel out because they appear in each moment function (e.g., Equations (34) and (35)).

This sensitivity analysis has shown that the absolute value of scattering using literature values of refractive index is probably within ±24% of the true value, while the precision is ±6%. Determination of a more accurate value requires detailed mass comparisons with filter measurements, although one needs to be mindful of intrinsic errors in gravimetric measurements. Park, Kittleson, and McMurry (Park, K., Kittelson, D., and McMurry, P., "A Closure Study of Aerosol Mass Concentration Measurements: Comparison of Values Obtained with Filters and by Direct Measurements of Mass Distributions," Atmospheric Environment 37: 1223-1230 (2003), which is incorporated herein by reference in its entirety) have performed detailed measurement comparisons of filter and other mobility methods, obtaining comparisons with a similar level of uncertainty, namely ±15-20%.

As previously mentioned, the STAR system can be implemented in a small package sampling instrument or as a non-intrusive, in-situ instrument with optics placed external to the particle flow. Those of ordinary skill in the art will know that finding the optimal geometry that allows measurements down to the minimum particle concentration level will depend on finding the best light collection angles, reducing stray light, and optimizing the electronics, using phase sensitive detection if necessary to extend the minimum size and concentration range.

Although typical embodiments and details have been explained hereinabove with the intention of illustrating several embodiments of the present invention, it is understood that several changes and variations in the methods, apparatuses, and systems disclosed herein may be implemented within the scope of the various embodiments of the present invention. Experiments performed using the above-noted approaches and apparatuses will now be summarized as exemplary embodiments of the subject matter contained herein.

2.0 Experimental Measurements 2.1 Relationship of Theory to Experimental Measurements STAR measurements have been obtained on both diesel and gas turbines. The theory of soot formation and scattering show that the fundamental theory is applicable to either combustion system. Measurements on a variety of fuels, laminar or turbulent research flames, and diesel engines show that the fundamental theory is correct, and that the fractal dimension, $D_f$, of soot agglomerates in the large particle limit is constant (1.7-1.9). It is also known that the agglomerate size distributions are self-preserving (see, for example, Sorensen, supra), forming clusters of primary particles that have a narrow range of scaling parameters (distribution widths). For measurement of the soot mass concentration, $C_m$, both the fractal dimension and the particle size distribution parameters are ratioed moment functions that can be integrated to form a nearly invariant function, $C_m\#$, that is dependent only on the measured scattering at two angles ratio if the fractal dimension and size distribution widths are relatively invariant. There has been a factor of two uncertainty about the absolute scattering constant, $k_o$, but recent experimental literature values are converging, and the recent STAR measurements disclosed herein are consistent with these measurements on flames and diesel engines. More significantly, an established, but overlooked theory, (1) shows that the value of $k_o$ can be derived theoretically, and consistent with a Gaussian cutoff function for the density correlation function and (2) predicts that $k_o$ is preferably 2.0, consistent with the recent measurements.

In the above-disclosed analysis, it has been shown that the overall soot property parameter, $S_p$ is nearly invariant, becoming more so for a limited class of combustors and fuels, such as gas turbines for typical operating fuel/air ratios. An exception is for large fuel/air equivalence ratios, according to DeCarlo, et al. (DeCarlo, P., Worsnop, D., Slowik, J., Davidovits, P., and Jimenez, J., "Particle Morphology and Density Characterization by Combined Mobility and Aerodynamic Diameter Measurements. Part 1, Theory," Aerosol Sci. and Tech., 38(12): 1185-1205 (2004), which is incorporated herein by reference in its entirety). Under extremely fuel rich conditions, rarely occurring in practice, the fractal dimension can increase significantly, to a value of 2.95, decreasing the $C_m\#$ by a factor of 2. Almost all practical combustion systems are tuned to operate at fuel/air equivalence ratios which are stoichiometric or fuel-lean. Other factors that are not consistent with black carbon soot can occur in engines and are related to the occurrence of lube-oil bypass and the generation of white smoke, i.e. moisture at cold start conditions. These conditions can be addressed by heating of the gas sample to drive water and oil condensates back into the gas phase so that they do not confuse the black carbon measurements.

2.2 Volkswagen Jetta Diesel

Figure 12:
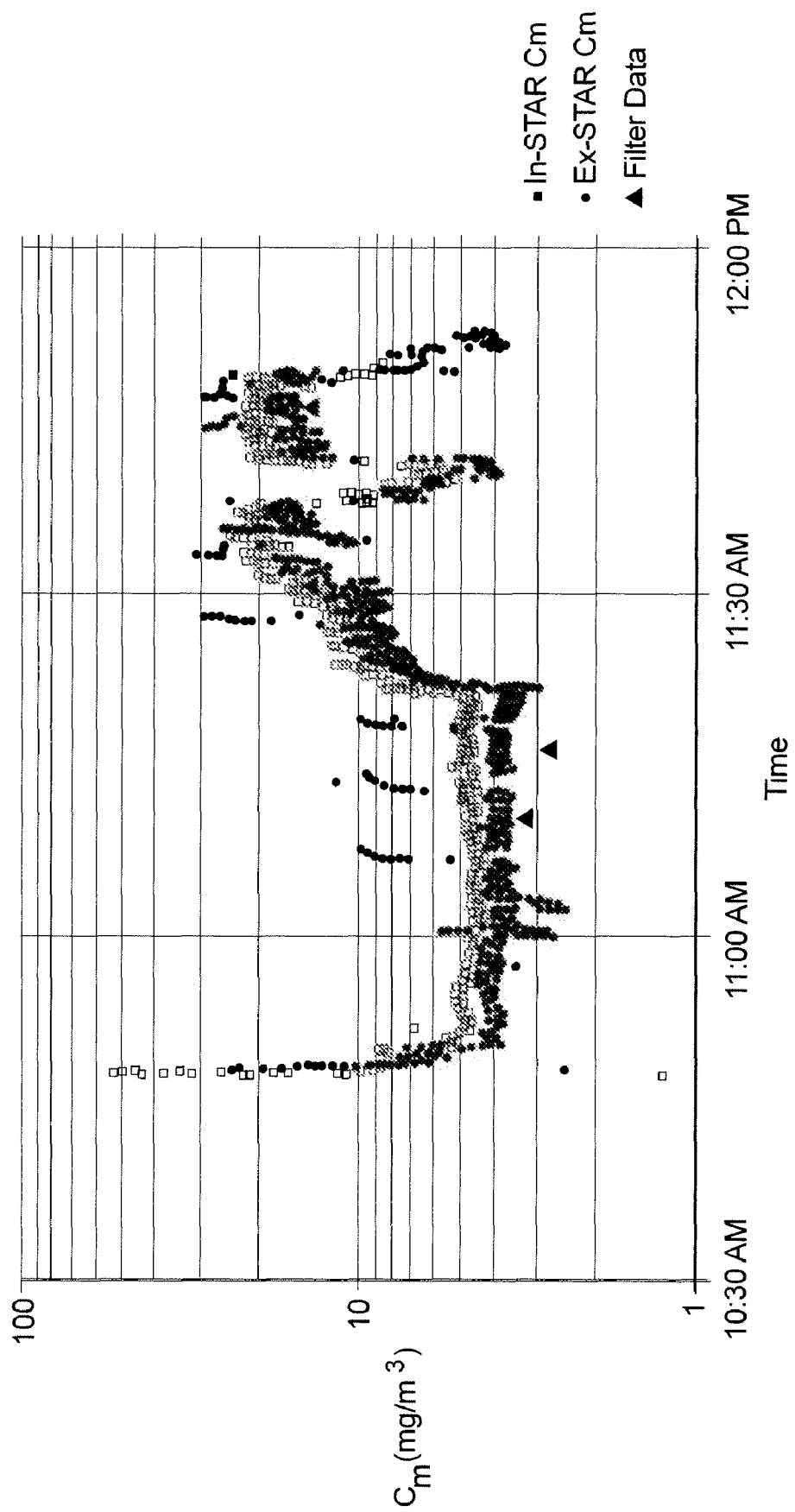
FIG. 12 illustrates a comparison of time-resolved VW Jetta Diesel exhaust measurements with in- and ex-STAR instruments and filter data.
Figure 13:
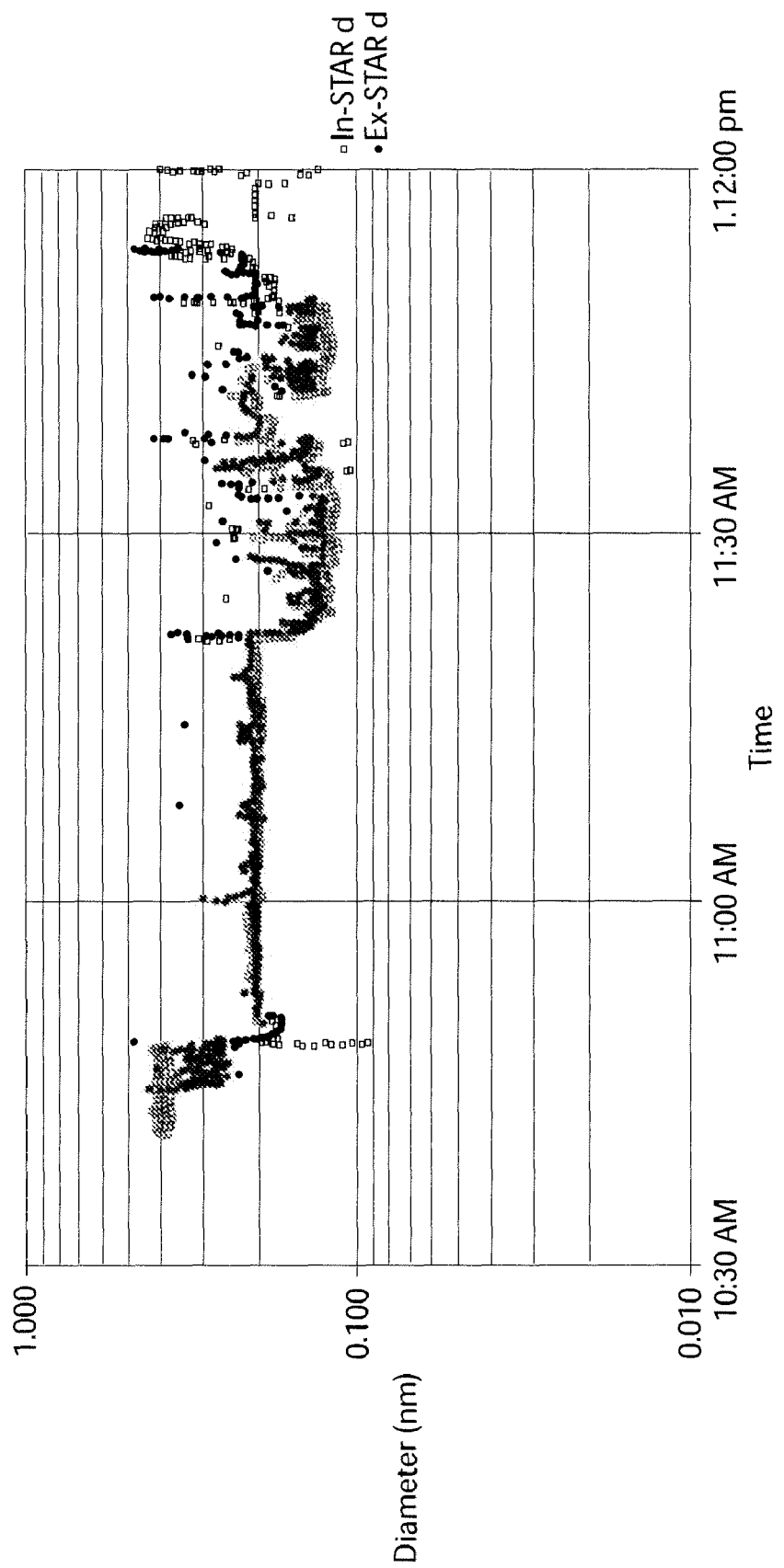
FIG. 13 illustrates a comparison of time-resolved exhaust measurements of agglomerate diameters for in- and ex-STAR instruments for a VW Jetta diesel at two different RPM settings.

This inventor has measured the exhaust at low (800 RPM) and high (2000 RPM) idle conditions for a VW Jetta Diesel as shown in FIGS. 12 and 13. These results show that the ex-STAR results are 17% lower than the in-situ measurements due to sample line losses in the 30 ft heated probe, and are consistent throughout all operating conditions. The ex-STAR measurements are 17% higher than the filter mass measurements on average, though closer at the higher RPM conditions. These results are within the estimated statistical error, given the uncertainties in soot and instrument parameters. The particle size measurements for the two instruments are in good agreement over all measurement conditions.

2.3 Repeat VW Jetta Diesel Measurements

Figure 14:
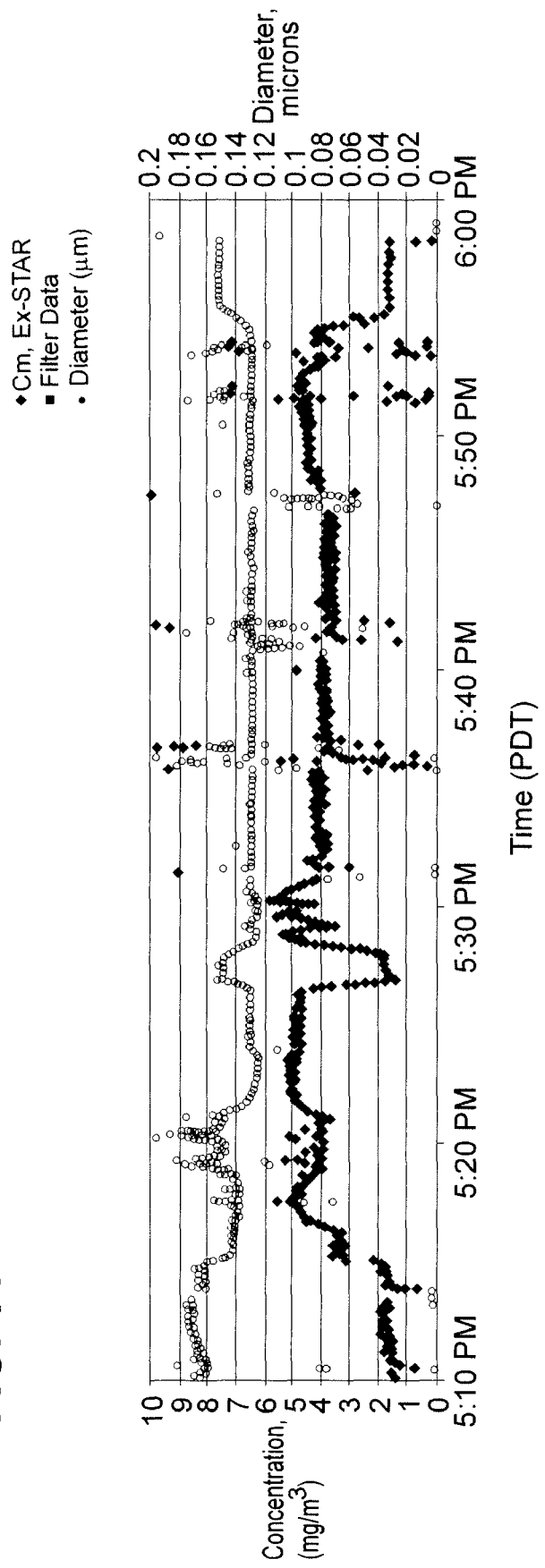
FIG. 14 illustrates a summary comparison of all VW diesel exhaust concentration results, comparing ex-STAR with filter sample measurements.

A second round of tests were used to confirm the initial round of VW Jetta measurements. First, it was confirmed that the detector calibrations using Rayleigh scattering from air had not changed. These results are shown in FIG. 14, which again show good agreement with filter sample measurements. It should be noted that while the accelerator position on the VW Jetta could be set, the Ignition Control Unit would vary the RPM and other engine conditions automatically, leading to some variation in the operating condition.

Figure 15:
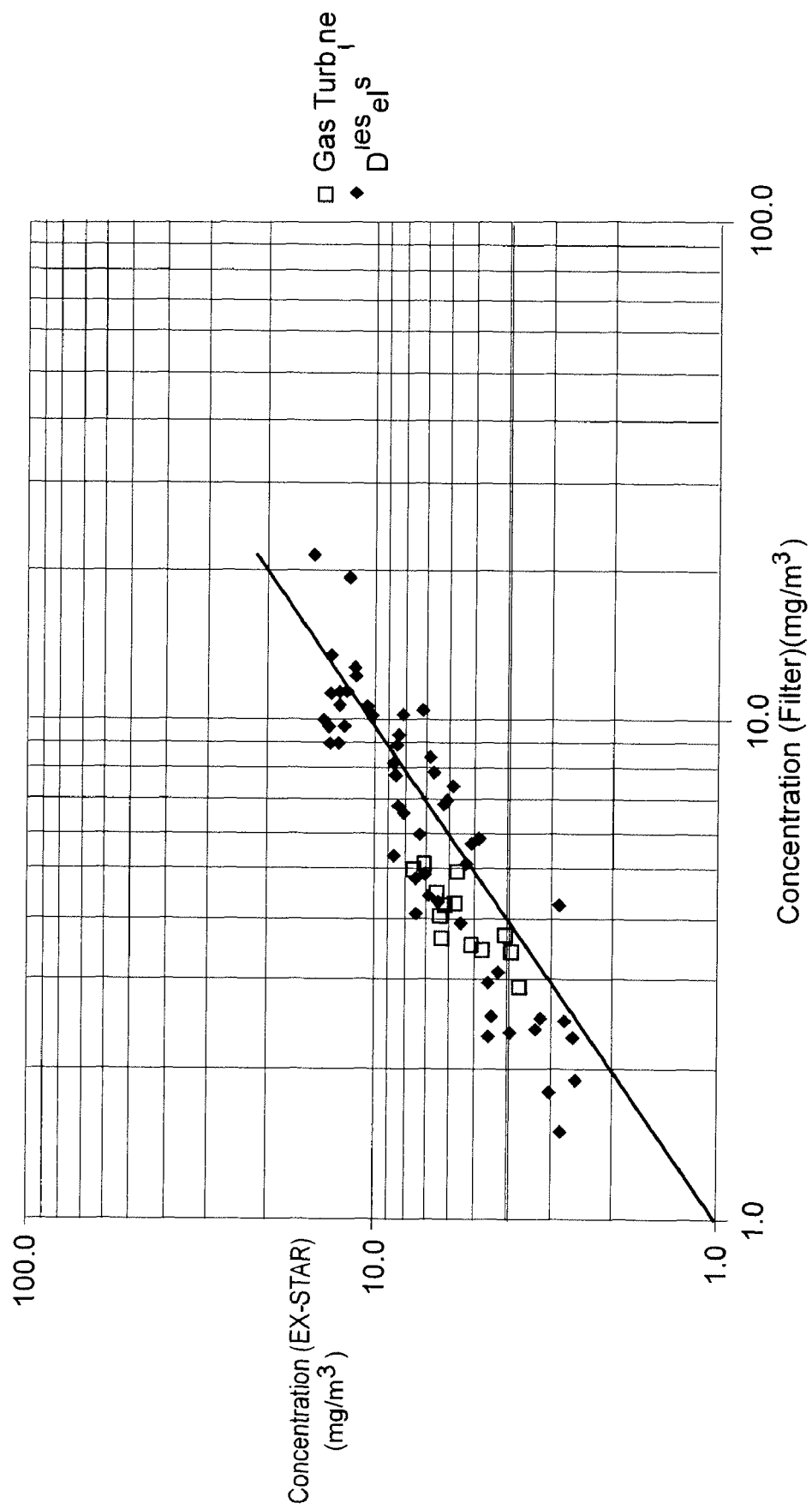
FIG. 15 illustrates a continuous time history of STAR measurements of particle size and concentration for a gas turbine compared with filter sample measurements.

Additional measurements were obtained on a Ford F250 diesel engine, and a gas turbine engine, and these results are summarized along with all previous VW Jetta measurements as shown in FIG. 15. These results show good correlation with independent mass filter measurements. It is noted that there does not appear to be any fundamental difference between diesel soots and those from gas turbines. As long as one measures the mean soot size in conjunction with the mass concentration, this appears to provide sufficient information. In all these measurements, standard soot property values derived from the literature have been used. The experimental results suggest that the soot property values for $f(m)/\rho_p$ or $d_p$ could be 15% higher, which is within the literature uncertainty for soot property values. As used herein throughout, the expressions "polydispersed agglomerate" or "a polydispersion of agglomerates" refer to agglomerates of various sizes.

Those of ordinary skill in the art will appreciate, after reviewing the subject matter disclosed herein, the fact that the quantity nS(q) in Equation (24) can be varied to give size information (Equation (14)) by modifying the parameter q. In the exemplary embodiments described hereinabove, choosing two different values of θ has varied q. Given that q=[4π sin(θ/2)]/λ, one can vary q in two ways, i.e., by either varying θ or by varying λ. Thus, it should be understood that apparatuses and methods that uses two wavelengths, a single detector, and the disclosed theoretical approach to obtain size information and concentration of a polydispersed agglomerate are also within the scope of the subject matter disclosed herein.

Figure 16:
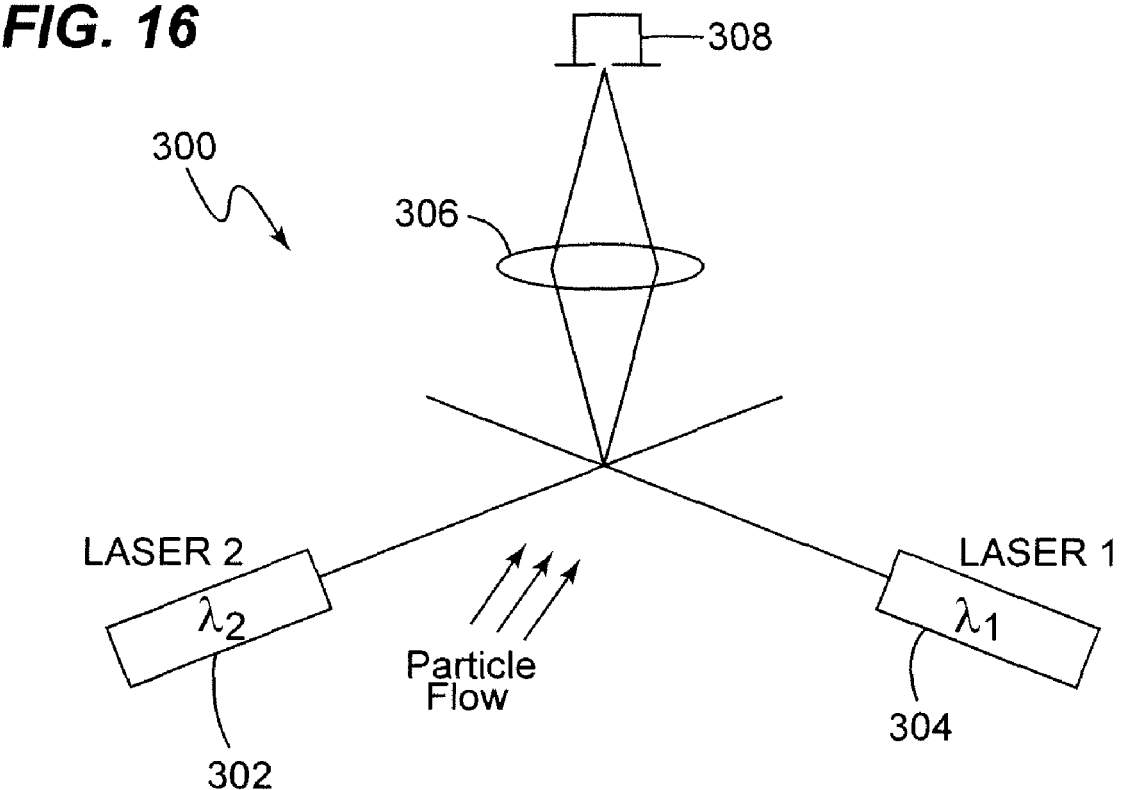
FIG. 16 illustrates a schematic diagram of a light scattering and detection geometry according to another embodiment of the subject matter disclosed.
Figure 17:
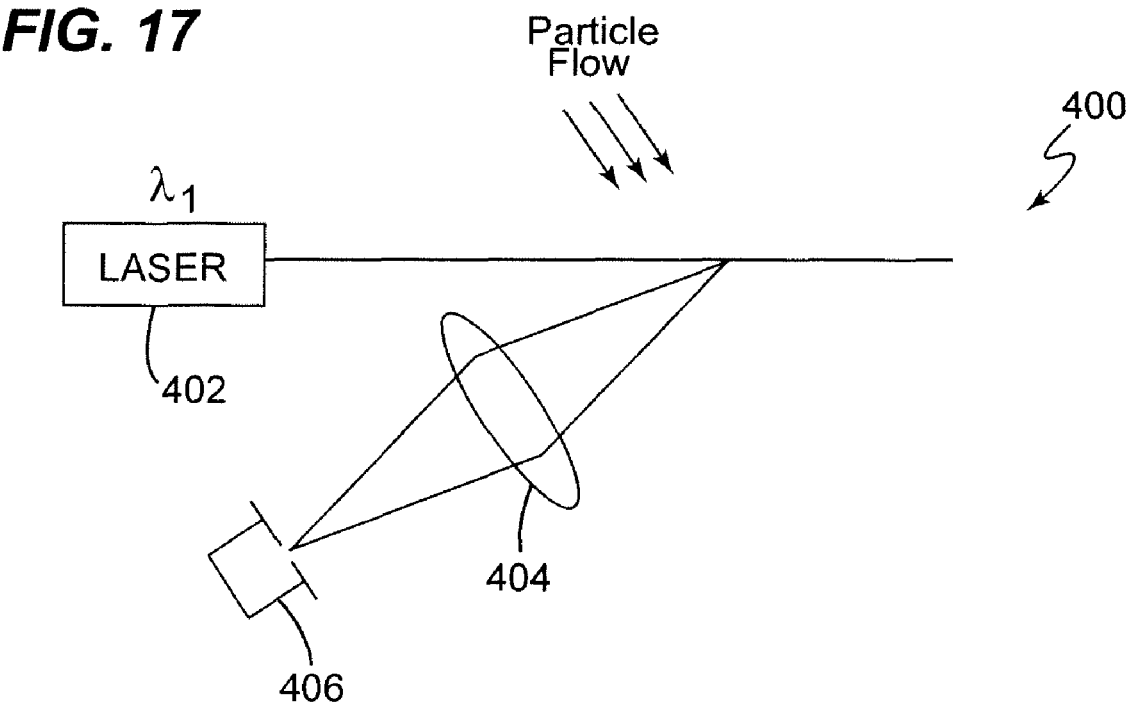
FIG. 17 illustrates a schematic diagram of a light scattering and detection geometry according to yet another embodiment of the subject matter disclosed.

For example, FIGS. 16 and 17 illustrate two exemplary schematic diagrams of light scattering and detection geometries according to yet other embodiments of the subject matter disclosed. In FIG. 16, a light scattering and detection geometry 300 for an apparatus for measuring average size and concentration of a polydispersed agglomerate of primary particles is disclosed in which a first light source 302 emits a first beam of light in a first direction, the first beam of light having a first wave length, $\lambda_1$. The light scattering an detection geometry 300 also includes a second light source 304 to emit a second beam of light in a second direction, the second beam of light having a second wave length, $\lambda_2$, different than the first wave length, $\lambda_1$. The light scattering and detection geometry 300 further includes a lens 306 to focus scattered light from the particles passing through a probe volume formed by the intersection of the light from the first and second sources 302 and 304 and a light detector 308 to generate a first signal proportional to light scattered from the first light source by the polydispersed agglomerate and to generate a second signal proportional to light scattered from the second light source by the polydispersed agglomerate. Based on the approached disclosed hereinabove, those of ordinary skill in the applicable arts will appreciate that for the light scattering an detection geometry 300 just described, the average concentration of the polydispersed agglomerate, $C_m$, per unit total scattered light, $P_{T\theta}$, is given by:

$$\frac{C_m}{P_{T\theta}} = g_1 g_2 C_m \#, \qquad (42)$$

where $g_1$ is a function of optical properties of the primary particles, $g_2$ is a function of a configuration of the apparatus, and $C_m\#$ is a nearly invariant function of the scattering ratio, $R_{\lambda 1/\lambda 2}$, of the first signal to the second signal. Although lens are illustrated in FIG. 16 to focus and/or collect scattered light, it should be understood that any light collecting device, including, but not being limited to, an elliptical mirror, may be used for the purpose of defining the probe volume, focusing the light from the light sources, and collecting the scattered light generated by the particles in the particle flow.

Analogous to Equations (33)-(35), in the light scattering and detection geometry 300, the following is an expression for $C_m\#$:

$$C_m\#(qd_{go}) \equiv \left(\frac{M_1}{M_{2\lambda 1}}\right) \frac{\left(\frac{2}{3\pi^3}\right)\left(\frac{\lambda_1}{d_p}\right)^{Df}}{n_o S(qd_{go})}, \qquad (43)$$

where $S(qd_{go})$ is a structure-correcting factor for the agglomerate particle and the non-dimensional first and second moment functions, $M_1$ and $M_{2\theta 1}$, are given by:

$$M_1 = \Sigma\left(\frac{\Delta N_i}{N_t}\right)\left(\frac{n_i}{n_{go}}\right) \qquad (44)$$

and $$M_{2\lambda 1} = \Sigma\left(\frac{\Delta N_i}{N_t}\right)\left(\frac{n_i}{n_{go}}\right)^2 \left(\frac{S(q_{\lambda 1} d_{gi})}{S(q_{\lambda 1} d_{go})}\right), \qquad (45)$$

where $\Delta N_i$ is the number of agglomerate particles in each subclass i, $n_i$ is the number of primary particles in each subclass, and $d_{gi}$ is an average gyration diameter for each subclass.

In the limiting case of large values of q, another apparatus 400 for measuring average mass concentration and size of a polydispersed agglomerate of primary particles is shown in FIG. 17. In the apparatus 400, a light source 402 is used to emit a beam of light in a first direction, the beam of light having a wave length in the ultraviolet to blue range. A lens 404 focus the scattered light from particles flowing through the beam of light emitted from the light source 402 and a light detector 406 generates a signal proportional to light scattered onto the light detector 406 by the polydispersed agglomerate in the probe volume formed in the beam of light. In the apparatus 400 of FIG. 17, the average mass concentration of the polydispersed agglomerate, $C_m$, per unit total scattered light, $P_{T\theta}$, is given by:

$$\frac{C_m}{P_{T\theta}} = f_1 f_2 C_m \#, \qquad (46)$$

where $f_1$ is a function of optical properties of the primary particles, $f_2$ is a function of a configuration of the apparatus, and $C_m\#$ is substantially constant, as explained hereinabove. As understood by those of ordinary skill in the arts, if a second detector is provided to the apparatus 400, particle size information would also be measurable with the apparatus 400.

A new light scattering analysis has been disclosed for interpreting two-angle measurements of black carbon soot to give values for the mass concentration and mean agglomerate particle size. One of the advantageous features for these methods and associated apparatuses and systems is that they express the results in terms of three primary elements, namely a soot property term, the instrument characteristics, and a new function ($C_m\#$) that is dependent only on the measured scattering signal ratio at two angles. The fundamental result that all three soot properties may be combined into one explicit product term, $S_p$, is significant because the primary uncertainty in using light scattering to measure accurate mass concentrations has been the variable range of soot refractive index and the primary particle size, $d_p$. The analysis and approach disclosed herein also allow one to eliminate a commonly used parameter, $k_o$, as an independent soot property, reducing the uncertainty in calculation of the mass concentration, $C_m$, in Equation (37). The disclosed analysis shows that three fundamental properties of primary particles, which have all been measured independently in the literature, may be related through the particle density in such a way that $S_p$ is generally invariant despite variations in the individual properties for different combustion conditions. Thus STAR can give accurate measurements without the need for specific engine/fuel correlation or calibration.

Recapitulating, measurements have been performed using both an in-situ STAR and a sampling version of STAR for a variety of diesel and gas turbines which show that one can obtain ±24% accuracy measurements using only currently available literature values for evaluating $S_p$. The precision (±6%) and speed (up to 100 Hz if necessary) of optical methods are good. A simple method has been developed for instrument verification and calibration based on measuring the Rayleigh scattering of air.

An apparatus for measuring mass mean particle size and concentration of a group of particles that includes a polydispersion of agglomerates (size range from 50-1000 nm) is within the scope of the various embodiments of the subject matter disclosed. These agglomerates may include smaller and nearly monomeric primary particles (size range of 10-50 nm). In one of the disclosed embodiments, the apparatus includes an illumination collimated laser source; two light detectors positioned to measure a light scattered when the group of particles moves past the illumination source; a DC (or average) calculating device to calculate a DC component of a signal produced by the light detector; size and concentration calculating device to calculate the mean size, and concentrations (mass, number, area) of the group of particles based at least on the DC components of the signal produced by the detector. In these apparatuses, the size and concentration calculating devices may further include a two-parameter mathematical expression modeling the size distribution of the group of particles. In one embodiment, this two-parameter mathematical expression is one of a log-normal distribution or scaling distribution.

In the above-summarized examples of an apparatus within the scope of the subject matter disclosed, the light scattering signals from the agglomerates can be related to the size and concentration by the calculating device expressed according to Equations (33), (36), and (37).

The $C_m\#$ uses the theoretical results from Nikolai (described above) for nS(q) for monomers to give a unique relationship similar to that shown in FIG. 9 for both monomers and polydisperse soot size distributions. This relationship will vary depending on the chosen angular positions of the two detectors, but provides a unique $C_m\#$ for the two specified detectors. These equations are valid for the agglomerates and monomers previously described.

In these apparatuses, a result of the size and concentration calculating device is expressed according to the above-noted equations. In the noted apparatuses, a mean particle size range from approximately 60 to approximately 1000 nm may be measured and the mentioned detectors may be positioned at an angle to an axis of the forward direction of the light beam of the illumination source varying between zero and 180 degrees. In one preferred embodiment, these angles are approximately 30 and 90 degrees. In other embodiments of the noted apparatuses, the DC calculating device may be integrated into a single calculating device to calculate the noted DC components. Yet in other embodiments, the DC, and size and concentration calculating devices are disposed and operate inside of a computer.

In yet other embodiments of the disclosed apparatuses, the illumination source further includes an optical system to collimate or focus a light of the illumination source into a probe volume and the light detector detects light scattered by the group of particles passing through the probe volume. The illumination source may be a laser.

After review of the subject matter disclosed hereinabove it will become clear to those of ordinary skill that methods to measure a mean particle size and concentration of a group of particles are within the scope of the subject matter disclosed. Such methods include the steps of providing an illumination source; providing two detectors positioned to measure light scattered when the group of particles moves past the illumination source; calculating two DC components of signals produced by each of the two detectors; calculating the average size and concentration of the group of particles based on the DC components of the signals produced by each of the two detectors. In one preferred embodiment, the calculation of the size and concentration of the group of particles further includes a two-parameter mathematical expression for modeling the size distribution of the group of particles. The two-parameter mathematical expression may be one of a log-normal distribution, or of any scaling distribution that is consistent with measured agglomerate distributions.

In a preferred embodiment of the above-summarized methods, the result of the calculation of the size and concentration is expressed according to Equations (33), (36), and (37).

As noted above, in another embodiment of the disclosed method, a particle size range from approximately 60 to approximately 1000 nm is measured. In addition, the provision of the detectors may further include positioning the detectors at any angle to an axis of the illumination source varying between zero and 180 degrees. Although, as explained hereinabove, a range of angles is within the scope of the disclosed embodiments of the subject matter disclosed, two angles of approximately 30 and 90 degrees are currently favored.

Methods of measuring average size and concentration of a polydispersed agglomerate are also within the scope of the subject matters disclosed herein. Such methods include the steps of emitting a beam of light from a light source in a first direction, focusing the beam of light from the light source so as to form a probe volume, measuring light scattered from the polydispersed agglomerate passing through the probe volume with a first light detector positioned at a first angular position, $\theta_1$, from the first direction of the beam of light, measuring light scattered from the polydispersed agglomerate passing through the probe volume with a second light detector positioned at a second angular position, $\theta_2$, from the first direction of the beam of light, and calculating an average concentration of the polydispersed agglomerate, $C_m$, per unit total scattered light, $P_{T\theta}$, as already explained hereinabove. Variations of these methods, based on the structural features and theories disclosed herein are also with the scope of the subject matters disclosed, as recited in the claims attached herein below.

While the disclosed embodiments of the subject matter described herein have been shown in the drawings and fully described above with particularity and detail in connection with several exemplary embodiments, it will be apparent to those of ordinary skill in the art that many modifications, changes, and omissions are possible without materially departing from the novel teachings, the principles and concepts set forth herein, and advantages of the subject matter recited in the appended claims. Hence, the proper scope of the disclosed innovations should be determined only by the broadest interpretation of the appended claims so as to encompass all such modifications, changes, and omissions. In addition, the order or sequence of any process or method steps may be varied or re-sequenced according to alternative embodiments. Finally, in the claims, any means-plus-function clause is intended to cover the structures described herein as performing the recited function and not only structural equivalents, but also equivalent structures.

APPENDIX A

Rosin Rammler and Lognormal Size Distribution Functions

A1.1 Rosin Rammler

The Rosin-Rammler distribution, (RR), has been shown to provide an accurate correlation for many fractal materials, and recently has been shown to have a fundamental physical fractal basis (see, for example, Brown, W. K., and Wohletz, K. "Derivation of the Weibull Distribution Based on Physical Principles and its Connection to the Rosin-Rammler and Lognormal Distributions," Journal of Applied Physics, 78(4): 2758-2763 (1995), which is incorporated herein by reference in its entirety). The total particle volume, area, or number distribution in any system can be related to two parameters of the RR, given by:

$$dv/d \ln D_v = p \exp(-D_v)^p, \quad (A1)$$

where $v = V/V_t$ is the non-dimensional volume concentration normalized by the total volume $V_t$ (gm/m$^3$), p is related inversely to the distribution width, (analogous to $1/\sigma$ for the log-normal distribution), and $D_v = d/d_{vo}$ is the non-dimensional diameter normalized by the volume mode value, $d_{vo}$ (cm). Typical values of p range from 1 to 3 for various milled materials. The total volume is related to a characteristic particle number for the RR distribution, $N_{vo}$ (#/cm$^3$), corresponding to the mode diameter $d_{vo}$, by the relation:

$$V_t = C_v = (\pi/6) N_{vo} d_{vo}^3. \quad (A2)$$

One can then define the number distribution, which is important for determining the scattering signal, which is based on the number distribution weighted by the scattered signal for each particle size.

The number frequency is then given by:

$$dn_v/d \ln D_v = p D_v^{p-3} \exp(-D_v)^p, \quad (A3)$$

where $n_v = N/N_{vo}$ is the normalized number concentration.

Note that this form effectively generates an inverse power law characteristic for particles smaller than the mode diameter, $d_{vo}$ with values of p<3. Since most distributions are relatively broad (i.e. p<3) this generates a somewhat curious characteristic, where the total number of particles will tend towards infinity if the RR were correct (even though the volume remains finite), as $D_v$ approaches zero. In fact, physical number distributions deviate from the number distribution form because surface effects dominate fractal effects for small particles, and the particle number ultimately becomes finite for all practical distributions.

A1.2 Log-Normal Size Distributions

Measurements of typical soot size distributions using Scanning Mobility Particle Sizers (SMPS) show good correlations with a two-parameter, log-normal distribution function as shown in FIG. A1. The equation for a log-normal distribution is given by:

$$d\Phi/d \ln d = \{1/(\sqrt{2\pi} \ln \sigma)\} \exp \{-[(\ln(d_\Phi/d_{\Phi o}))^2/2 \ln^2 \sigma]\}, \quad (A4),$$

where $\Phi$ is equal to $N/N_t$ (non-dimensional particle number) or $V/V_t$ (non-dimensional particle volume), $N_t$ is equal to the total particle number concentration (#/cm$^3$), $V_t$ is equal to the total particle volume concentration (gm/cm$^3$), $\sigma$ is equal to the geometric distribution width given by $\sqrt{(d_{84}/d_{16})}$, which is the same for number or mass, and $d_{\Phi o}$ is equal to the geometric mean (mode, median) diameter for number or volume distribution.

Because in one preferred embodiment the median volume gyration diameter, $d_{gvo}$, is used as the characteristic agglomerate dimension, equations are developed for the number frequency which can be expressed in terms of volume median (equal to a log-normal mode) diameter. The total volume concentration can be given in terms of the mode diameter by the same relationship as for the RR distribution in Equation (A2). By integrating the volume-weighted distribution, one can obtain another relationship relating $N_{vo}$ to the total particle number concentration as follows:

$$N_t/N_{tv} = \{\exp(4.5 \ln^2 \sigma)\}. \quad (A5)$$

There is also a relationship between the number and mass geometric mean diameters (based on gyration diameters) given by, $$d_{ngo}/d_{vgo} = \{\exp(-3 \ln^2 \sigma)\}. \quad (A6)$$

One can use the equations above to express the number frequency in a form where the normalizing diameter is $d_{vgo}$ ($D_{vgo} = d_g/d_{vgo}$), and the normalizing number is $N_{tv}$ ($n_v = N/N_{tv}$), that is:

$$dn_{vg}/d \ln D_{vgo} = \{1/(\sqrt{2\pi} \ln \sigma)\} \exp\{-[((\ln D_{vgo})^2/2 \ln^2 \sigma) + 3 \ln D_{vgo}]\}. \quad (A7)$$

This relationship for the number frequency and the volume frequency of Equation (A6) can then be compared directly to the Rosin Rammler distributions, as shown in FIGS. A2 and A3. As described above, the RR form does not have a finite value of total particle number ($N_t$) for values of p<3, in contrast to the LN form, which is always finite. Nevertheless the distribution shapes are relatively similar for diameters >$d_{vgo}$. The primary difference is the asymmetry in the "tails" of the RR distributions, which decrease more slowly for small diameters, and fall off more quickly for large diameters.

Thus for both the number and mass distributions with six free parameters, the additional equations above reduce the number of independently chosen distribution parameters to three, namely $\sigma$ (or p), $d_{\Phi o}$, and $M_t$. One has two independent measurables, so that one should typically specify a value for the distribution width, $\sigma$ (or p), which can be obtained from SMPS measurements. The question remains as to the sensitivity of the data interpretation to typical values of the distribution width. Although there does not appear to be a major difference in the mass distributions between the RR and LN distribution forms, FIG. A3 shows differences in the number distribution for values of d<$d_o$. These differences may be reflected in evaluation of the mass and scattering integrals, $M_1$ and $M_2$, which use the number distribution in the computation. Because the weighting function, F(d), increases rapidly ($d^4-d^2$) with particle size for both these integrals, the upper end of the size distribution contributes more to the evaluation of the integrals. Given the similar overlap above do for the RR and LN distributions for the range of $\sigma$ and p that apply to typical soot distributions, there is not a large variation in evaluation of the scattering integrals. Moreover, these variations tend to ratio out in the expressions for $d_o$ and $C_m$, as shown for log-normal distributions in Appendix B.

APPENDIX B

Distribution Width and Fractal Dimension Sensitivity

This inventor has performed limited numerical estimates of the sensitivity of the $C_m\#$ to the effects of uncertainty of the distribution width $\sigma$ and fractal dimension $D_f$. The numerical calculations showed minimal variation with the typical range of published values for σ and $D_f$, which is consistent with the results found by De Luliis, et al., supra. For a more general estimate, one can derive an approximate analytical expression, sufficient for an upper-bound sensitivity analysis.

There is an exact solution to the moment integrals, i.e.: as noted by Wang and Sorensen, supra, that is:

$$M_n = \int D_n^i p(D_n^i) dD_n = c\exp[(i+1)^2(\ln^2\sigma)/2] \quad (B1)$$

for number distribution-based moments, $[D_n=(d/d_{on})]$, and $$M_v = c\exp[(i-3)^2(\ln^2\sigma)/2] \quad (B2)$$

for volume distribution-based moments, where $[D_m=(d/d_{ov})]$.

The first moment (mass) using this formula is exact, where $i=D_f$, while for the second moment (scattering) integral, i ranges effectively from $2D_f$ at $d/d_{ov}=1$, to $D_f$ for $d/d_{ov}>15$. The approximate power variation is due to the effect of the structure function S(qd) in Equation (15) of the main text.

To determine the sensitivity to variations in the distribution width for volume distributions one computes the ratio of first and second moments, $$M_{1v}/M_{2v} = \exp[(0.5 \ln^2\sigma)\{(D_f-3)^2-(aD_f3)^2\}], \quad (B3)$$

where "a" ranges from 2 to 1 with increasing $d_v$, approximating the product of $\{d_v^{Df} S(qd_v)\}$ inside the second moment integral. The computed values of the maximum moment ratio values are similar to the exact values, based on a simple power law approximation, allowing one to place an upper bound on the variation with distribution width, σ. This inventor uses a median value of σ=1.75, based on experimental mobility measurements, and if one assumes a range of σ=1.6-1.9, Equation (B3) gives a variation of less than ±5% for $D_f=1.8$-2.27 and $d_{vo}>60$ nm. Thus sensitivity to knowledge of the exact agglomerate size distribution width is minimal. This is a useful result for validating the accuracy of the STAR measurements without the need for knowledge of the detailed agglomerate size distribution information.

One can also place an upper bound estimate on sensitivity of the $C_m$# to the measured range of fractal dimensions for both the small particle range $(d_m/d_p)<4k_o^{2.12}$, and the large particle range, $(d_m/d_p)>4k_o^{2.12}$, where $k_o$ is now known from Nicolai, et al., supra, to be a constant=2.0. The uncertainty in each range is approximately $D_f=\pm7\%$. Again, for $d_{vgo}>60$ nm, the uncertainty in the $C_m$# is approximately the same as the uncertainty in $D_f$, decreasing with increasing mobility diameter.

APPENDIX C

Extinction Measurements

Filter Absorption (FA) measurements (Aethelometer and MAAP for black carbon) provide another optical method for measuring soot concentrations. The FA approach is relatively simple and an attractive method for quasi-real-time mass sampling measurements. The STAR method, however, has the advantage of obtaining real-time mean agglomerate size measurements, and can also be configured for in situ measurements. Similar to STAR, one of the instrument parameters needed is the specification of the light absorption coefficient. Again, a range of values are given in the literature, although a more limited set has been recommended, ranging from $\sigma_e=6.1$-8.3 $m^2/gm$ (see, for example, Petzold, A and Schonlinner, M., "Multi-angle Absorption Photometry—A New Method for Measurement of Aerosol Light Absorption and Atmospheric Black Carbon," Journal of Aerosol Science, 35(4): 421-441 (2004) and Kreidenweis, S., "Effects of Mixing on Extinction by Carbonaceous Particles," Journal of Geophysical Research, 104(D13): 15941-15954 (1999), both of which are incorporated herein by reference in their entirety). To compare scattering results with absorption on an equal basis, it would be useful to know the refractive index on which this empirical value is based. From RDG theory there is a simple relationship for the absorption coefficient, $$\sigma_a = 6\pi E(m)/\rho_p\lambda. \quad (C1)$$

The extinction coefficient is given by, $$\sigma_e = \sigma_a/(1-\rho_{se}), \quad (C2)$$

where the scattering/extinction ratio (albedo) $\rho_{se}$ is approximately constant in the range of 0.2-0.25 (see, for example, Zhu, J., Choi, M., Mulholland, G., and Gritzo, L, "Soot Scattering Measurements in the Visible and Near-infrared Spectrum," Proceedings of the Combustion Institute, Vol 28, p. 439-446, 2000, which is incorporated herein by reference in its entirety). For filter absorption measurements, the mass concentration is given by:

$$C_m = A_f/(\sigma_e V_s)(-\ln(I/I_o)), \quad (C3)$$

where, $A_f$ is the collection filter area ($cm^2$), $V_s$ is the gas sample volume ($cm^3$), and $I/I_o$ is the light transmittance through the sample.

Elemental carbon has a maximum particle density of 2.0 $gm/cm^3$, so this places an upper bound on primary particle soot density. Recent measurements indicate that the primary particle soot density is on the order of 1.7 $gm/cm^3$, although it is unclear whether this is elemental carbon. Most probable values of E(m) (from Sorensen, supra, and Table I) indicate E(m) is in the range of 0.25 to 0.36. The laser wavelength used for the Multi-angle absorption photometer, (MAAP) manufactured by Thermo Electron, is λ=0.67 μm. For the APEX experiment, Aerodyne and NASA Lewis researchers used an attenuation coefficient of 6.1 $m^2/g$, which empirically accounts for non-ideal scattering/attenuation effects from the filter itself along with unknown absorption and scattering properties of atmospheric or spark discharged black carbon (see, for example, Petzold and Schonlinner, supra).

There is an uncertainty of which density is associated with a given refractive index, although E(m) is known to be proportional to the density, Equation (24). Therefore the ratio E(m)/$\rho_p$ is essentially a fundamental constant for elemental carbon and thus $\sigma_a$ is independent of variations in refractive index and primary particle density for actual soot particles. Using the optical properties (m=1.7–0.7i) and density ($\rho_p$=2.0 $gm/cm^3$) for elemental carbon, or the most probable values for soot refractive index along with a lower density, $\sigma_e=5.1$ $m^2/g$ for λ=0.67 μm, approximately 20% lower than that used in the MAAP measurements. Thus to compare STAR measurements with MAAP filter absorption measurements on an equivalent basis, one should increase MAAP results by 20%.

Following the same rationale for STAR, this inventor chooses a value for f(m) used in the scattering measurements, based on the fundamental refractive index of elemental carbon. This inventor also uses the density associated with elemental carbon (2.0 μM/$cm^3$) to compute the ratio f(m)/$\rho_p$. A value of $\rho_p$=1.7 as the reference value for comparing the density correlation as a function of agglomerate mobility diameter has also been used. In effect, a more likely value for soot of f(m)=0.26 is being chosen, with a density=1.7 $gm/cm^3$, similar to choosing the mean value for (Y.

In both cases, the ratios E(m)/$\rho_p$ and f(m)/$\rho_p$, have been evaluated based on elemental carbon, which gives an upper bound for both these optical properties, and thus a lower bound on $C_m$, for both absorption and scattering measurements.

What is claimed is:

1. An apparatus for measuring average size and concentration of a polydispersed agglomerate of primary particles, the apparatus comprising:
   a light source configured to emit a beam of light in a first direction;
   a first light detector positioned at a first angular position, $\theta_1$, from the first direction of the beam of light, the first light detector being configured to generate a first signal proportional to light scattered onto the first light detector by the polydispersed agglomerate in a probe volume formed in the beam of light; and
   a second light detector positioned at a second angular position, $\theta_2$, from the first direction of the beam of light, the second light detector being configured to generate a second signal proportional to light scattered onto the second light detector by the polydispersed agglomerate in the probe volume, wherein an average concentration of the polydispersed agglomerate, $C_m$, per unit total scattered light, $P_{T\theta}$, is given by:

$$\frac{C_m}{P_{T\theta}} = f_1 f_2 C_m \#,$$

where $f_1$ is a function of optical properties of the primary particles, $f_2$ is a function of a configuration of the apparatus, and $C_m\#$ is a nearly invariant first function of a scattering ratio, $R_{\theta 1/\theta 2}$, of the first signal to the second signal.

2. The apparatus according to claim 1, wherein the average size of the polydispersed agglomerate is calculated from a variation of an average gyration diameter, $d_{go}$, for an assumed size distribution for the polydispersed agglomerate as a nearly invariant second function of the scattering ratio.

3. The apparatus according to claim 2, wherein the polydispersed agglomerate is soot.

4. The apparatus according to claim 2, wherein the first angular position is in the range of 0 to 180 degrees from the forward direction of the beam of light and the second angular position is in the range of 0 to 180 degrees from the forward direction of the beam of light, the first angular position being larger that the second angular position.

5. The apparatus according to claim 4, wherein the first angular position is about 90 degrees from the forward direction of the beam of light and the second angular position is about 30 degrees from the forward direction of the beam of light.

6. The apparatus according to claim 5, wherein, for $R_{90/30}$ less than 40% and $d_{go}$ greater than 150 μm, $C_m\#$ is substantially constant.

7. The apparatus according to claim 6, wherein a critical value of the gyration diameter for a substantially constant $C_m\#$ decreases as the wavelength of the light decreases and the light scattering angle increases.

8. The apparatus according the claim 2, wherein the assumed agglomerate size distribution is selected from the group consisting of a log-normal distribution, a scaling distribution, a Rosin-Rammler distribution, and a Weibull distribution.

9. The apparatus according to claim 1, further comprising:
   an optical element to focus the beam of light from the light source so as to form the probe volume; and
   an optical receiver element disposed between the probe volume and the first light detector.

10. The apparatus according to claim 9, wherein the optical element and the optical receiver element are, respectively, a focusing lens and a receiver lens.

11. The apparatus according the claim 9, wherein the optical element and the optical receiver element are, respectively, a focusing elliptical mirror and a receiver elliptical mirror.

12. The apparatus according to claim 9, wherein $$f_1 = \left(\frac{\rho_p}{d_p^{3-D_f} f(\underline{m})}\right),$$

$$f_2 = \left(\frac{\lambda^{4-D_f}}{P_l l \Omega}\right),$$

$$C_m\# = C_m\#(qd_{go}), \text{ and}$$

$$\frac{C_m}{P_{T\theta}} = \left(\frac{\rho_p}{d_p^{3-D_f} f(\underline{m})}\right)\left(\frac{\lambda^{4-D_f}}{P_l l \Omega}\right) C_m\#(qd_{go}),$$

where $d_p$ is a diameter of the primary particle, $\rho_p$ is a density of the primary particle, $D_f$ is a fractal dimension, $\underline{m}$ is a complex refractive index of the primary particle, $f(\underline{m})$ is a scattering refractive index function, $\Omega$ is a scattered light collection aperture of the optical receiver element, $P_l$ is the power of the light source, $l$ is a length of the probe volume, $q$ is a scattering wave vector at a mean scattering angle, $\theta$, for the optical receiver element given, in terms of a wave length, $\lambda$, of the light emitted by the light source, by $(4\pi/\lambda)\sin(\theta/2)$, and $d_{go}$ is an average gyration diameter for an assumed size distribution for the polydispersed agglomerate.

13. The apparatus according to claim 12, wherein $d_{go}$ is calculated as a nearly invariant second function of the scattering ratio.

14. The apparatus according to claim 12, wherein $$C_m\#(qd_{go}) \equiv \left(\frac{M_1}{M_{2\theta 1}}\right) \frac{\left(\frac{2}{3\pi^3}\right)\left(\frac{\lambda}{d_p}\right)^{D_f}}{n_o S(qd_{go})},$$

where $S(qd_{go})$ is a structure-correcting factor for the agglomerate and the non-dimensional first and second moment functions, $M_1$ and $M_{2\theta 1}$, are given by:

$$M_1 = \Sigma\left(\frac{\Delta N_i}{N_t}\right)\left(\frac{n_i}{n_{go}}\right)$$

and $$M_{2\theta} = \Sigma\left(\frac{\Delta N_i}{N_t}\right)\left(\frac{n_i}{n_{go}}\right)^2 \left(\frac{S(q_\theta d_{gi})}{S(q_\theta d_{go})}\right),$$

where $\Delta N_i$ is the number of agglomerate particles in each subclass $i$, $n_i$ is the number of primary particles in each subclass, and $d_{gi}$ is an average gyration diameter for each subclass.

15. The apparatus according to claim 14, wherein the average gyration diameter, $d_{go}$, is implicitly related to the scattering ratio of the first and second signals for the polydisperson agglomerate through the first and second moments and structure functions, $S(qd_{go})$, by $$R_{\theta 1/\theta 2} = \left(\frac{M_{2\theta 1}}{M_{2\theta 2}}\right)\left(\frac{S(q_{\theta 1}d_{go})}{S(q_{\theta 2}d_{go})}\right).$$

16. The apparatus according the claim 1, wherein, for a wavelength of the light in the ultraviolet to blue range and for the first angular position greater than 90 degrees, for mass concentration measurements, only the scattered light detected by the first light detector is used.

17. The apparatus according to claim 1, wherein the first or second detectors are selected from the group consisting of a photomultiplier tube, a Silicon diode, and an avalanche photodiode.

18. The apparatus according to claim 1, wherein the first signal or the second signal is an average of a time varying signal dependent on a size of the agglomerates, their location in the probe volume, and the number of agglomerates in the probe volume.

19. The apparatus according to claim 1, wherein a mean size of the polydispersed agglomerate ranges from about 60 to about 1000 nm.

20. The apparatus according to claim 19, wherein the polydispersed agglomerate includes substantially monomeric primary particles in the size range of about 10 to about 50 nm.

21. The apparatus according to claim 19, wherein the polydispersed agglomerate mean size ranges from approximately 60 to approximately 400 nm.

22. The apparatus according to claim 1, wherein the light source is polarized.

23. The apparatus according to claim 1, wherein the light source is unpolarized.

24. The apparatus according to claim 1, wherein the polydispersed agglomerate is brought to the probe volume via an extractive sample line.

25. The apparatus according to claim 1, wherein the size and concentration of the polydispersed agglomerate are measured in-situ.

26. An apparatus selected from the group consisting of a diesel engine, a gasoline engine, a propulsion gas turbine engine, a power generating gas turbine engine, a locomotive, and an off-highway vehicle, said apparatus comprising the apparatus for measuring average size and concentration of the polydispersed agglomerate of primary particles according to claim 1.

27. A method of measuring average size and concentration of a polydispersed agglomerate, the method comprising:
   emitting a beam of light from a light source in a first direction;
   measuring light scattered from the polydispersed agglomerate passing through a probe volume formed by the beam of light with a first light detector positioned at a first angular position, $\theta_1$, from the first direction of the beam of light;
   measuring light scattered from the polydispersed agglomerate passing through the probe volume with a second light detector positioned at a second angular position, $\theta_2$, from the first direction of the beam of light; and
   calculating, using a processor, an average concentration of the polydispersed agglomerate, $C_m$, per unit total scattered light, $P_{T\theta}$, using the following equation:

$$\frac{C_m}{P_{T\theta}} = f_1 f_2 C_m\#,$$

where $f_1$ is a function of primary particle optical properties, $f_2$ is a function of a configuration of the apparatus, and $C_m\#$ is a nearly invariant first function of a ratio, $R_{\theta 1/\theta 2}$, of the scattered light measured by the first light detector to the scattered light measured by the second detector.

28. The method according to claim 27, further comprising:
   calculating the average size of the polydispersed agglomerate based on an average gyration diameter, $d_{go}$, for an assumed size distribution for the polydispersed agglomerate using a nearly invariant second function of the scattering ratio.

29. The method according to claim 27, wherein $$f_1 = \left(\frac{\rho_p}{d_p^{3-D_f} f(\underline{m})}\right),$$

$$f_2 = \left(\frac{\lambda^{4-D_f}}{P_l l \Omega}\right),$$

$$C_m\# = C_m\#(qd_{go}), \text{ and}$$

$$\frac{C_m}{P_{T\theta}} = \left(\frac{\rho_p}{d_p^{3-D_f} f(\underline{m})}\right)\left(\frac{\lambda^{4-D_f}}{P_l l \Omega}\right) C_m\#(qd_{go}),$$

where $d_p$ is a diameter of the primary particle, $\rho_p$ is a density of the primary particle, $D_f$ is a fractal dimension, $\underline{m}$ is a complex refractive index of the primary particle, $f(\underline{m})$ is a scattering refractive index function, $\Omega$ is a scattered light collection aperture of a receiver lens, $P_l$ is the power of the light source, l is a length of the probe volume, q is a scattering wave vector at a mean scattering angle, $\theta$, for the receiver lens given, in terms of a wave length, $\lambda$, of the light emitted by the light source, by $(4\pi/\lambda)\sin(\theta/2)$, and $d_{go}$ is an average gyration diameter for an assumed size distribution for the polydispersed agglomerate.

30. The method according to claim 29, further comprising:
   calculating the average size of the polydispersed agglomerate based on an average gyration diameter, $d_{go}$, for an assumed size distribution for the polydispersed agglomerate using a nearly invariant second function of the scattering ratio.

31. The method according to claim 29, wherein $$C_m\#(qd_{go}) \equiv \left(\frac{M_1}{M_{2\theta 1}}\right)\frac{\left(\frac{2}{3\pi^3}\right)\left(\frac{\lambda}{d_p}\right)^{D_f}}{n_o S(qd_{go})},$$

where $S(qd_{go})$ is a structure-correcting factor for the polydispersed agglomerate and the non-dimensional first and second moment functions, $M_1$ and $M_{2\theta 1}$, are given by:

$$M_1 = \Sigma\left(\frac{\Delta N_i}{N_t}\right)\left(\frac{n_i}{n_{go}}\right)$$

and

-continued $$M_{2\theta} = \Sigma\left(\frac{\Delta N_i}{N_t}\right)\left(\frac{n_i}{n_{go}}\right)^2\left(\frac{S(q_\theta d_{gi})}{S(q_\theta d_{go})}\right),$$

where $\Delta N_i$ is the number of agglomerate particles in each subclass i, $n_i$ is the number of primary particles in each subclass, and $d_{gi}$ is an average gyration diameter for each subclass.

32. The method according to claim 31, wherein the average gyration diameter, $d_{go}$, is implicitly related to the scattering ratio of the first and second signals for the polydisperson agglomerate through the first and second moments and structure functions, $S(qd_{go})$, by $$R_{\theta1/\theta2} = \left(\frac{M_{2\theta1}}{M_{2\theta2}}\right)\left(\frac{S(q_{\theta1}d_{go})}{S(q_{\theta2}d_{go})}\right).$$

33. The method according to claim 27, wherein the first angular position is in the range of 0 to 180 degrees from the forward direction of the beam of light and the second angular position is in the range of 0 to 180 degrees from the forward direction of the beam of light, the first angular position being larger than the second angular position.

34. The method according to claim 33, wherein the first angular position is about 90 degrees from the forward direction of the beam of light and the second angular position is about 30 degrees from the forward direction of the beam of light.

35. The method according to claim 34, wherein, for $R_{90/30}$ less than 40% and $d_{go}$ greater than 150 μm, $C_m\#$ is substantially constant.

36. The method according to claim 35, wherein a critical value of the gyration diameter for a substantially constant $C_m\#$ decreases as the wavelength of the light decreases.

37. The method according the claim 27, wherein, for a wavelength of the light in the ultraviolet to blue range and for a first angular position of the first light detector greater than 90 degrees, for accurate mass concentration measurements, only the scattered light detected by the first light detector is measured.

38. The method according to claim 27, wherein the first or second detectors are selected from the group consisting of a photomultiplier tube, a Silicon diode, and an avalanche photodiode.

39. The method according to claim 27, wherein the first angular position is different than the second angular position.

40. The method according to claim 27, wherein the first signal or the second signal is an average of a time varying signal dependent on a size of the agglomerates, their location in the probe volume, and the number of agglomerates in the sample volume.

41. The method according to claim 27, wherein a mean size of the polydispersed agglomerate ranges from about 60 to about 1000 nm.

42. The method according to claim 41, wherein the polydispersed agglomerate includes substantially monomeric primary particles in the size range of about 10 to about 50 nm.

43. The method according to claim 41, wherein the mean size of the polydispersed agglomerate ranges from approximately 60 to approximately 400 nm.

44. The method according to claim 27, wherein the light source is polarized.

45. The method according to claim 27, wherein the light source is unpolarized.

46. The method according the claim 28, wherein the assumed agglomerate size distribution is selected from the group consisting of a log-normal distribution, a scaling distribution, a Rosin-Rammler distribution, and a Weibull distribution.

47. The method according to claim 27, wherein the polydispersed agglomerate is brought to the probe volume via an extractive sample line.

48. The method according to claim 27, wherein the size and concentration of the polydispersed agglomerate are measured in-situ.

49. The method according to claim 27, wherein the polydispersed agglomerate is soot from an exhaust of an apparatus selected from the group consisting of a diesel engine, a gasoline engine, a propulsion gas turbine engine, a power generating gas turbine engine, a locomotive, and an off-highway vehicle.

* * * * *